United States Patent
Hu et al.

(10) Patent No.: US 12,056,211 B2
(45) Date of Patent: Aug. 6, 2024

(54) METHOD AND APPARATUS FOR DETERMINING IMAGE TO BE LABELED AND MODEL TRAINING METHOD AND APPARATUS

(71) Applicant: TENCENT TECHNOLOGY (SHENZHEN) COMPANY LIMITED, Shenzhen (CN)

(72) Inventors: Yifan Hu, Shenzhen (CN); Yuexiang Li, Shenzhen (CN); Yefeng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 195 days.

(21) Appl. No.: 17/501,899

(22) Filed: Oct. 14, 2021

(65) Prior Publication Data

US 2022/0036135 A1 Feb. 3, 2022

Related U.S. Application Data

(63) Continuation of application No. PCT/CN2020/106541, filed on Aug. 3, 2020.

(30) Foreign Application Priority Data

Aug. 29, 2019 (CN) .......................... 201910820773.7

(51) Int. Cl.
*G06V 20/70* (2022.01)
*A61B 6/00* (2024.01)
(Continued)

(52) U.S. Cl.
CPC ........ *G06F 18/2155* (2023.01); *A61B 6/5294* (2013.01); *G06F 18/2178* (2023.01);
(Continued)

(58) Field of Classification Search
CPC .......... G06N 3/045; G06N 3/08; G06N 20/00; G06N 20/20; G06N 3/0464; G06N 3/09;
(Continued)

(56) References Cited

U.S. PATENT DOCUMENTS 10,610,098 B1* 4/2020 Soliz .................... G06V 40/197
2018/0144243 A1* 5/2018 Hsieh ..................... G06F 11/30
(Continued)

FOREIGN PATENT DOCUMENTS

| CN | 104392456 A | 3/2015 |
| CN | 107103187 A | 8/2017 |

(Continued)

OTHER PUBLICATIONS

Zhao et al., Versatile Framework for Medical Image Processing and Analysis with Application to Automatic Bone Age Assessment, Dec. 31, 2018 [retrieved May 25, 2023], Journal of Electrical and Computer Engineering, vol. 2018, Article ID 2187247, 14 pages. (Year: 2018).*

(Continued)

*Primary Examiner* — Matthew C Bella
*Assistant Examiner* — Dennis Rosario
(74) *Attorney, Agent, or Firm* — ANOVA LAW GROUP, PLLC

(57) ABSTRACT

A method for determining a target image to be labeled includes: obtaining an original image and an autoencoder (AE) set, the original image being an image having not been labeled, the AE set including N AEs; obtaining an encoded image set corresponding to the original image by using the AE set, the encoded image set including N encoded images, the encoded images being corresponding to the AEs; obtaining the encoded image set and a segmentation result set corresponding to the original image by using an image segmentation network, the image segmentation network (Continued)

including M image segmentation sub-networks, and the segmentation result set including [(N+1)*M] segmentation results; determining labeling uncertainty corresponding to the original image according to the segmentation result set; and determining whether the original image is a target image according to the labeling uncertainty.

16 Claims, 12 Drawing Sheets

(51) Int. Cl.
    *G06F 18/21*     (2023.01)
    *G06F 18/214*     (2023.01)
    *G06N 3/0455*     (2023.01)
    *G06T 7/10*     (2017.01)
    *G06T 7/143*     (2017.01)
    *G06T 9/00*     (2006.01)
    *G06V 20/69*     (2022.01)

(52) U.S. Cl.
    CPC ............ *G06N 3/0455* (2023.01); *G06T 7/10* (2017.01); *G06T 7/143* (2017.01); *G06T 9/002* (2013.01); *G06V 20/695* (2022.01); *G06V 20/70* (2022.01); *G06T 2207/20112* (2013.01); *G06T 2207/30004* (2013.01); *G06T 2219/004* (2013.01)

(58) Field of Classification Search
CPC .......... G06N 3/0455; G06N 3/04; G06N 3/02; G06N 3/0895; G06N 3/088; G06T 2207/20081; G06T 2207/20084; G06T 7/11; G06T 7/0012; G06T 2207/10081; G06T 2207/30096; G06T 2207/10088; G06T 2207/10132; G06T 2207/30004; G06T 7/10; G06T 7/194; G06T 7/12; G06T 3/4046; G06T 9/002; G06T 5/60; G06T 7/215; G06T 2207/20112; G06T 2207/20128; G06T 2207/30024; G06T 2207/10056; G06T 2207/10104; G06T 2207/10072; G06T 2210/41; G06T 2211/40; G06T 2207/30041; G06T 2207/30061; G06T 2207/10108; G06T 2207/30081; G06T 11/003; G06T 2207/10068; G06T 2207/30008; G06T 2207/30068; G06T 2207/10101; G06T 2207/10136; G06T 2207/10112; G06T 2207/30012; G06T 2207/10092; G06T 2207/10121; G06T 2207/30032; G06T 2207/30064; G06T 2219/004; G06V 10/82; G06V 2201/03; G06V 10/454; G06V 10/26; G06V 20/70; G06V 10/7753; G06V 10/778; G06V 10/7784; G06V 10/7788; G06V 10/7792; G06V 10/7796; G06V 20/695; G06V 20/49; G06V 20/69; G16H 30/40; G16H 30/20; G06F 18/2155; G06F 2207/4824; A61B 5/7264; A61B 5/7267; A61B 5/005; A61B 6/032; A61B 6/504; A61B 6/5294; A61B 1/000096; A61B 5/0077; A61B 5/0044; A61B 5/0042; A61B 5/004; A61B 5/0033; A61B 5/0035; A61B 5/0037; A61B 5/0036; A61B 2090/3762; A61B 2090/376; A61B 90/37; A61B 6/037; A61B 8/13; A61B 5/1128; A61B 2090/367; A61B 2090/3966; A61B 2576/026; A61B 2576/023; A61B 2576/02; A61B 2576/00; A61B 3/12; A61B 3/14; A61B 5/0073; A61B 8/4483; A61B 8/466; A61B 8/5207; A61B 8/5261; A61B 8/0825; A61B 5/0066; A61B 6/025; A61B 6/03; A61B 6/5002; A61B 6/5229; A61B 2090/374; A61B 6/482; A61B 6/486; A61B 5/0515; A61B 5/066

See application file for complete search history.

(56) References Cited

U.S. PATENT DOCUMENTS

2019/0130279 A1     5/2019   Beggel et al.
2021/0398282 A1*  12/2021  Frank ....................... G06T 3/40

FOREIGN PATENT DOCUMENTS

| CN | 109102495 A | 12/2018 |
| CN | 110009598 A | 7/2019 |
| CN | 110070540 A | 7/2019 |
| CN | 110517759 A | 11/2019 |

OTHER PUBLICATIONS

[item U continued] Retrieved: https://www.hindawi.com/journals/jece/2018/2187247/ (Year: 2018).*
Blanch, Active Deep Learning for Medical Imaging Segmentation (Thesis), 2017 (issued) [retrieved May 25, 2023], Universitat Politecnica De Catalunya BarcelonaTech, 45 pages. Retrieved: https://upcommons.upc.edu/handle/2117/109304 (Year: 2017).*
Wang et al., Uncertainty-Guided Domain Alignment for Layer Segmentation in OCT Images, Aug. 22, 2019 [retrieved Dec. 4, 2023], Cornell University:arXiv, version 1, 9 pages. Retrieved: https://arxiv.org/abs/1908.08242v1 (Year: 2019).*
Laves et al., A dataset of laryngeal endoscopic images with comparative study on convolution neural network-based semantic segmentation, Published: Jan. 16, 2019, Issued: Mar. 14, 2019 [retrieved Dec. 4, 2023], International Journal of Computer Assisted Radiology and Surgery, vol. 14, Issue 3, pp. 483-492. (Year: 2019).*
[item V continued] Retrieved: https://link.springer.com/article/10.1007/s11548-018-01910-0 (Year: 2019).*
Kendall et al., What Uncertainties Do We Need in Bayesian Deep Learning for Computer Vision?, Oct. 5, 2017 [retrieved Dec. 4, 2023], Cornell University:arXiv, version 2, pp. 1-12. Retrieved: https://arxiv.org/abs/1703.04977 (Year: 2017).*
He et al., Autoencoder based self-supervised test-time adaptation for medical image analysis, Aug. 2021: on-line: Jun. 19, 2021 [ retrieved Mar. 18, 2024], Medical Image Analysis, vol. 72, 13 pages. Retrieved: https://www.sciencedirect.com/science/article/pii/S1361841521001821 (Year: 2021).*
The World Intellectual Property Organization (WIPO) International Search Report for PCT/CN2020/106541 Nov. 11, 2020 6 Pages (including translation).

* cited by examiner

METHOD AND APPARATUS FOR DETERMINING IMAGE TO BE LABELED AND MODEL TRAINING METHOD AND APPARATUS

CROSS-REFERENCES TO RELATED APPLICATIONS

The present disclosure is a continuation application of PCT Patent Application No. PCT/CN2020/106541, entitled "METHOD AND APPARATUS FOR DETERMINING IMAGE TO BE MARKED, AND METHOD AND APPARATUS FOR TRAINING MODEL" and filed on Aug. 3, 2020, which claims priority to Chinese Patent Application No. 201910820773.7, entitled "METHOD AND APPARATUS FOR DETERMINING TO-BE-LABELED IMAGE AND MODEL TRAINING METHOD AND APPARATUS" and filed with the China National Intellectual Property Administration on Aug. 29, 2019, the entire contents of both of which are incorporated herein by reference.

FIELD OF THE TECHNOLOGY

The present disclosure relates to the field of Artificial Intelligence (AI), and in particular, to an image processing technology.

BACKGROUND OF THE DISCLOSURE

A medical image refers to an image of an internal tissue of a human body or a part of the human body obtained in a non-invasive manner for medical treatment or medical research, and is an important means and reference factor for assisting clinical diagnosis. The intrinsic heterogeneities of different diseases are also reflected in imaging phenotypes of the diseases. Therefore, it is the most challenging task in medical image analysis to diagnose etiology or segment lesions by using medical images.

Deep convolutional neural network algorithms have been widely used in the classification and segmentation of lesions. Most of the classical segmentation and classification methods require high-precision label, so a lot of time is required for labeling. At present, a method of adding a dropout layer to the segmentation task is proposed to obtain segmentation results and various uncertainty. Images with high uncertainty can be labeled.

However, there is a problem in extracting uncertainty based on the dropout mechanism that: the dropout mechanism is obtained based on networks with similar structures and the same input image, and although different nodes are used each time, parameters of a large number of nodes are the same. Therefore, the output results have high correlation, and it is difficult to process images into results with huge differences, resulting in the lack of rationality of uncertainty calculation, which is not conducive to the selection of accurate to-be-labeled images.

SUMMARY

Embodiments of the present disclosure provide a method and apparatus for determining a to-be-labeled image and a model training method and apparatus. Different autoencoders (AEs) focus on extracting information of an original image from different aspects, and the understanding of different AEs on the original image is differentiated. In addition, output results of different AEs are applied to different image segmentation sub-networks, which will make the output results more varied, so as to improve the calculation rationality of uncertainty, thereby helping to select more accurate to-be-labeled images.

One aspect of the present disclosure provides a method for determining a target image to be labeled, performed by a computing device, the method including: obtaining an original image and an AE set, the original image being an image having not been labeled, the AE set including N AEs, N being a positive integer; obtaining an encoded image set corresponding to the original image by using the AE set, the encoded image set including N encoded images, the encoded images being corresponding to the AEs; obtaining the encoded image set and a segmentation result set corresponding to the original image by using an image segmentation network, the image segmentation network including M image segmentation sub-networks, and the segmentation result set including [(N+1)*M] segmentation results, M being a positive integer; determining a labeling uncertainty corresponding to the original image according to the segmentation result set; and determining whether the original image is a target image according to the labeling uncertainty.

Another aspect of the present disclosure provides a server, including: a memory, a transceiver, a processor, and a bus system. The memory is configured to store a program. The processor is configured to execute the program in the memory, including the following operations: obtaining an original image and an AE set, the original image being an image having not been labeled, the AE set including N AEs, N being a positive integer; obtaining an encoded image set corresponding to the original image by using the AE set, the encoded image set including N encoded images, the encoded images being corresponding to the AEs; obtaining the encoded image set and a segmentation result set corresponding to the original image by using an image segmentation network, the image segmentation network including M image segmentation sub-networks, and the segmentation result set including [(N+1)*M] segmentation results, M being a positive integer; determining a labeling uncertainty corresponding to the original image according to the segmentation result set; and determining whether the original image is a target image according to the labeling uncertainty. The bus system is configured to connect the memory and the processor, to cause the memory to communicate with the processor.

Another aspect of the present disclosure provides a non-transitory computer-readable storage medium, storing instructions, the instructions, when run on a computer, causing the computer to perform: obtaining an original image and an AE set, the original image being an image having not been labeled, the AE set including N AEs, N being a positive integer; obtaining an encoded image set corresponding to the original image by using the AE set, the encoded image set including N encoded images, the encoded images being corresponding to the AEs; obtaining the encoded image set and a segmentation result set corresponding to the original image by using an image segmentation network, the image segmentation network including M image segmentation sub-networks, and the segmentation result set including [(N+1)*M] segmentation results, M being a positive integer; determining a labeling uncertainty corresponding to the original image according to the segmentation result set; and determining whether the original image is a target image according to the labeling uncertainty.

As can be seen from the foregoing technical solutions, the embodiments of the present disclosure have the following advantages:

An embodiment of the present disclosure provides a method for determining a to-be-labeled image. First, an original image and an AE set are obtained, the original image being an image having not been labeled; then an encoded image set corresponding to the original image is obtained by using the AE set, the encoded image set including N encoded images, the encoded images being corresponding to AEs; then the encoded image set and a segmentation result set corresponding to the original image are obtained by using an image segmentation network, the image segmentation network including M image segmentation sub-networks, and the segmentation result set including [(N+1)*M] segmentation results; and finally uncertainty corresponding to the original image is determined according to the segmentation result set, the uncertainty being used for determining whether the original image is a to-be-labeled image. By means of the foregoing method, the original image is changed by using AEs based on different encoding policies. Different AEs can focus on extracting information of the original image from different aspects, to differentiate the understanding of different AEs on the original image, so that some parts after the reconstruction are similar while the other parts vary in details. In addition, output results of different AEs are applied to different image segmentation sub-networks, which will make the output results more varied, so as to improve the calculation rationality of uncertainty, thereby helping to select more accurate to-be-labeled images.

DESCRIPTION OF EMBODIMENTS

Figure 1:
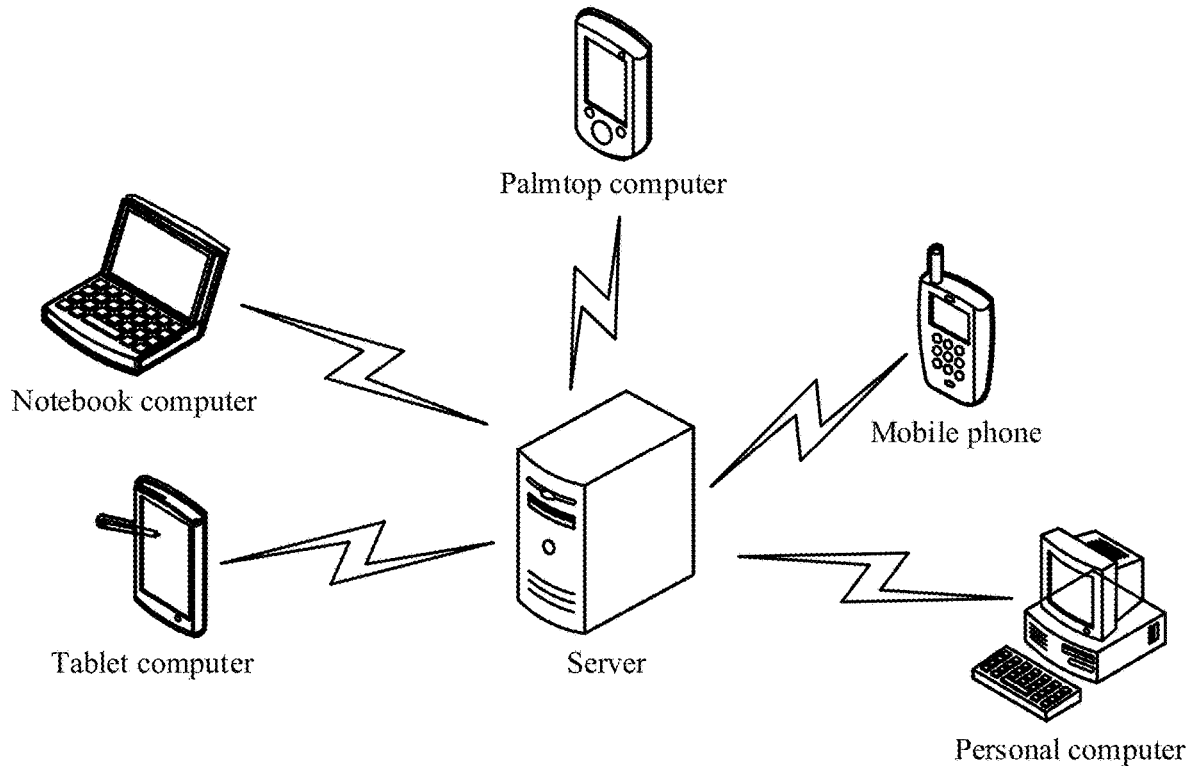
FIG. 1 is a schematic architectural diagram of a system for determining a to-be-labeled image according to an embodiment of the present disclosure.

Embodiments of the present disclosure provide a method and apparatus for determining a to-be-labeled image and a model training method and apparatus. Different AEs can focus on extracting information of an original image from different aspects, and the understanding of different AEs on the original image is differentiated. In addition, output results of different AEs are applied to different image segmentation sub-networks, which will make the output results more varied, so as to improve the calculation rationality of uncertainty, thereby helping to select more accurate to-be-labeled images. A to-be-labeled image may be referred to as a target image that require manual labeling of a user, and an uncertainty of automatic labeling (e.g., marking, classification, segmentation) performed by a machine learning algorithm may be high.

The terms such as "first", "second", "third", and "fourth" (if any) in the specification and claims of the present disclosure and in the accompanying drawings are used for distinguishing similar objects and not necessarily used for describing any particular order or sequence. It may be understood that the data termed in such a way is interchangeable in proper circumstances, so that the embodiments of the present disclosure described herein, for example, can be implemented in other sequences than the sequence illustrated or described herein. In addition, the terms "include", "corresponding to" and any other variants are intended to cover the non-exclusive inclusion. For example, a process, method, system, product, or device that includes a series of steps or units is not necessarily limited to those expressly listed steps or units, but may include other steps or units not expressly listed or inherent to such a process, method, product, or device.

It is to be understood that the method for determining a to-be-labeled image provided in the present disclosure has great application prospect. By using a small data set to learn and identify uncertainty of data, users can be helped to select more meaningful data for deep convolutional neural networks, which can add data that is not present in a training set, and then the data is labeled. In this way, greater training and testing accuracy can be achieved with a smaller amount of label.

Specifically, in the present disclosure, uncertainty of an image is calculated based on an AI technology, so as to use the uncertainty to select a to-be-labeled image. AI is a theory, method, technology and application system that uses digital computers or machines controlled by digital computers to simulate, extend and expand human intelligence, perceive the environment, acquire knowledge, and use knowledge to obtain the best results. In other words, AI is a comprehensive technology in computer science and attempts to understand the essence of intelligence and produce a new intelligent machine that can react in a manner similar to human intelligence. AI is to study design principles and implementation methods of various intelligent machines, to enable the machines to have functions of perception, reasoning, and decision-making.

The AI technology is a comprehensive discipline and relates to a wide range of fields including both hardware-level technologies and software-level technologies. Basic AI technologies generally include technologies such as a sensor, a dedicated AI chip, cloud computing, distributed storage, a big data processing technology, an operating/interaction system, and electromechanical integration. AI software technologies mainly include several major directions such as a computer vision (CV) technology, a speech processing technology, a natural language processing technology, and machine learning (ML)/deep learning.

In the present disclosure, an AE and an image segmentation model are trained in an ML manner. ML is a multi-field interdiscipline, and relates to a plurality of disciplines such as the probability theory, statistics, the approximation theory, convex analysis, and the algorithm complexity theory. ML specializes in studying how a computer simulates or implements a human learning behavior to obtain new knowledge or skills, and reorganize an existing knowledge structure, so as to keep improving its performance. ML is a core of the AI, is a basic way to make the computer intelligent, and is applied to various fields of the AI. ML and deep learning generally include technologies such as an artificial neural network, a belief network, reinforcement learning, transfer learning, inductive learning, and learning from demonstrations.

For ease of understanding, the present disclosure provides a method for determining a to-be-labeled image, and the method is applied to a system for determining a to-be-labeled image shown in FIG. 1. FIG. 1 is a schematic architectural diagram of a system for determining a to-be-labeled image according to an embodiment of the present disclosure. As shown in FIG. 1, a terminal device obtains a large quantity of medical images, and these medical images include, but are not limited to, images generated by medical instruments, such as computed tomography (CT) images, magnetic resonance imaging (MRI) images, ultrasound (B ultrasound, color Doppler ultrasound, cardiac color ultrasound, and three-dimensional color ultrasound) images, X-ray images, electrocardiogram, electroencephalogram, and optical photography images. The medical instruments include, but are not limited to, X-ray imaging instruments, CT, MRI, electrocardiogram and electroencephalogram instruments, and the like. A medical image is an important means and reference factor for assisting clinical diagnosis. The intrinsic heterogeneities of different diseases are also reflected in imaging phenotypes (appearances and shapes) of the diseases. Medical images captured by medical instruments may be stored in the terminal device.

The terminal device includes, but is not limited to, a tablet computer, a notebook computer, a palmtop computer, a mobile phone, a speech interaction device, and a personal computer (PC), and is not limited herein.

A large quantity of medical images can be seen by using the terminal device, and it takes a lot of time to label all these medical images. Therefore, it is necessary to select medical images with relatively high uncertainty from the large quantity of medical images for labeling. The terminal device transmits a large quantity of medical images to a server, so that the server calculates uncertainty of the medical images by using a plurality of AEs and a plurality of image segmentation networks, and labels medical images with relatively high uncertainty.

Figure 2:
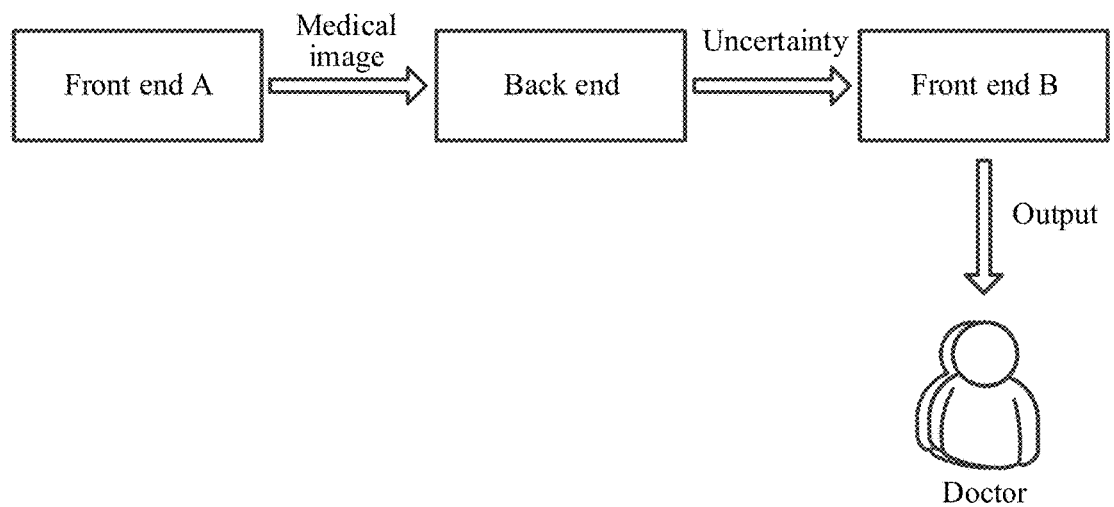
FIG. 2 is a schematic flowchart of determining a to-be-labeled image according to an embodiment of the present disclosure.

FIG. 2 is a schematic flowchart of determining a to-be-labeled image according to an embodiment of the present disclosure. As shown in FIG. 2, specifically, during model training, a front end A may receive labeled medical images and unlabeled medical images, and uploads these medical images to a back end after a preprocessing algorithm. It may be understood that, the preprocessing algorithm includes, but is not limited to data augmentation algorithms such as translation, rotation, and symmetry. The back end performs training by using the preprocessed labeled medical images to calculate uncertainty of unlabeled medical images, and then outputs the uncertainty to a front end B, and a doctor may select data with relatively high uncertainty by using the front end B for labeling.

The back end may be a server or a server cluster. During prediction, the back end may alternatively be a terminal device having a computing capability, for example, a computer. The front end A may be a medical instrument, or may be a terminal device storing medical images, for example, may be a computer. The front end B may be a terminal device, for example, a computer.

Figure 3:
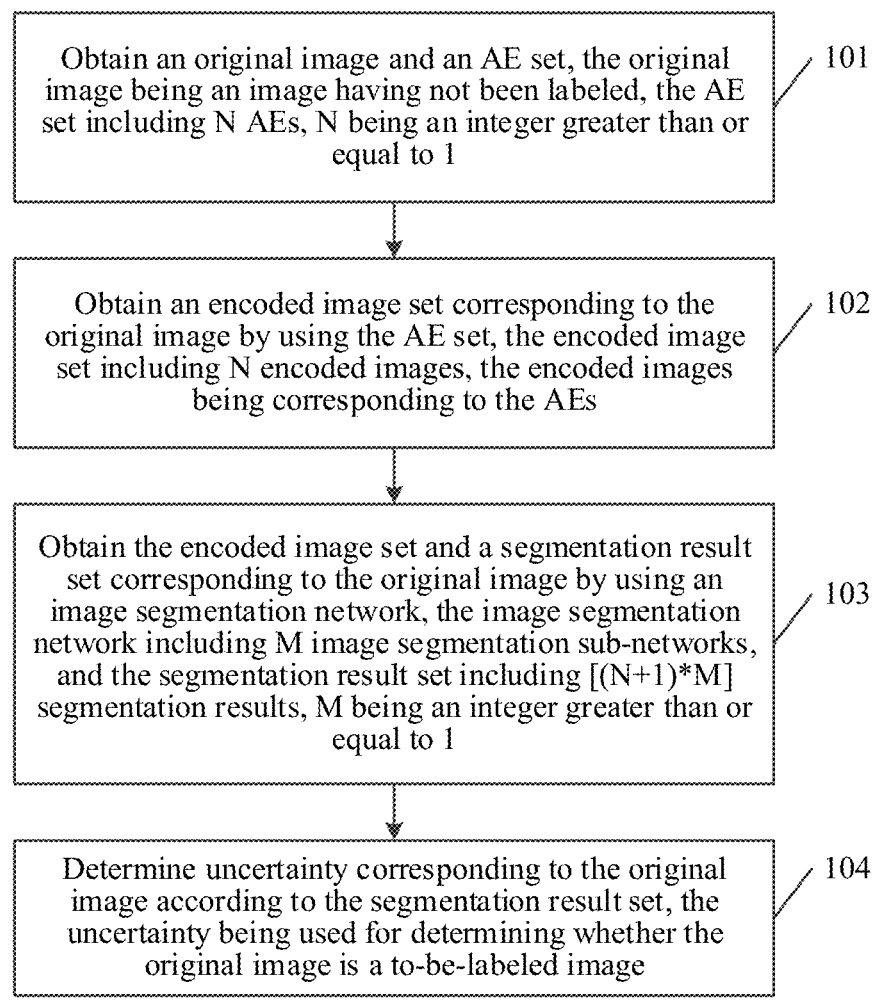
FIG. 3 is a schematic diagram of an embodiment of a method for determining a to-be-labeled image according to an embodiment of the present disclosure.

The method for determining a to-be-labeled image in the present disclosure is introduced below with reference to the foregoing introduction. Referring to FIG. 3, the method for determining a to-be-labeled image provided in this embodiment of the present disclosure relates to technologies such as AI image processing, and is specifically described by using the following embodiments:

101: Obtain an original image and an AE set, the original image being an image having not been labeled, the AE set including N AEs, N being an integer greater than or equal to 1.

In this embodiment, an apparatus for determining a to-be-labeled image obtains an original image and an AE set. It may be understood that, the apparatus for determining a to-be-labeled image is usually deployed on a server, or may be deployed on a server cluster, or may be deployed on a terminal device having a relatively strong computing capability. An example in which the apparatus is deployed on a server is used in the present disclosure for description, but it is not to be understood as a limitation to the present disclosure.

The original image may be a medical image, and include but not limited to a CT image, an MRI image, an ultrasound image, an X-ray image, an electrocardiogram, and an electroencephalogram. Alternatively, the original image may be an image of another type, for example, a surveillance image. An example in which the original image is a medical image is used for description in the present disclosure, but it is not to be understood as a limitation to the present disclosure.

An AE is a type of artificial neural network (ANN) used in semi-supervised learning and unsupervised learning, and its function is to perform representation learning on input information by using the input information as a learning target.

An AE includes an encoder and a decoder. According to learning paradigm, AEs may be divided into an undercomplete AE, a regularized AE, and a variational AE. The undercomplete AE and the regularized AE are discriminative models, and the variational AE is a generation model. According to construction type, the AE may be a neural network of a feedforward structure or a recursive structure. The AE has the function of representing learning algorithm in general sense, and is applied in dimensionality reduction and anomaly detection. An AE constructed with convolutional layers can be applied to CV problems, including image denoising, neural style transfer, and the like.

102: Obtain an encoded image set corresponding to the original image by using the AE set, the encoded image set including N encoded images, the encoded images being corresponding to the AEs.

In this embodiment, the apparatus for determining a to-be-labeled image obtains an encoded image set corresponding to the original image by using an AE set. The original image is an image having not been labeled, and the AE set includes N AEs. The original image is inputted into the N AEs separately to obtain the N encoded images. For ease of understanding, Table 1 schematically shows a correspondence among an input image, an AE, and an output image (that is, an encoded image).

TABLE 1

| Input | AE | Output |
| --- | --- | --- |
| Original image | AE A | Encoded image 1 |
| Original image | AE B | Encoded image 2 |
| Original image | AE C | Encoded image 3 |
| Original image | AE D | Encoded image 4 |
| Original image | AE F | Encoded image 5 |

As can be seen, the encoded images are in one-to-one correspondence with the AEs. The AE may extract different reconstruction information from an inputted original image, where the reconstruction information is reconstruction image information that is similar to the original image and that is generated by the AEs based on an encoding-decoding structure from images generated by AEs defined by different loss functions, and an encoded image is obtained.

103: Obtain the encoded image set and a segmentation result set corresponding to the original image by using an image segmentation network, the image segmentation network including M image segmentation sub-networks, and the segmentation result set including [(N+1)*M] segmentation results, M being an integer greater than or equal to 1.

In this embodiment, the apparatus for determining a to-be-labeled image uses the N encoded images and the original image as an input of the image segmentation network. The image segmentation network includes M image segmentation sub-network, and therefore, [(N+1)*M] segmentation results are obtained. For ease of understanding, Table 2 schematically shows a correspondence among an input image, an image segmentation sub-network, and an output image (that is, a segmentation result).

TABLE 2

| Input | Image segmentation sub-network | Output |
| --- | --- | --- |
| Original image | Image segmentation sub-network A | Segmentation result 1 |
| Encoded image 1 | Image segmentation sub-network A | Segmentation result 2 |
| Encoded image 2 | Image segmentation sub-network A | Segmentation result 3 |
| Original image | Image segmentation sub-network B | Segmentation result 4 |
| Encoded image 1 | Image segmentation sub-network B | Segmentation result 5 |
| Encoded image 2 | Image segmentation sub-network B | Segmentation result 6 |

As can be seen, it is assumed that there are two encoded images, that is, N=2, both the original image and the two encoded images are used as an input of the image segmentation sub-network A, and the image segmentation sub-network A outputs corresponding segmentation results respectively, that is, three segmentation results are obtained. Similarly, both the original image and the two encoded images are used as an input of the image segmentation sub-network B, and the image segmentation sub-network B outputs corresponding segmentation results respectively, that is, three segmentation results are obtained. Therefore, six segmentation results are obtained in total, that is, [(N+1)*M]=[(2+1)*2]=6.

A plurality of different unsupervised image segmentation sub-networks may be used to extract bottom expression information of an image, so that different unsupervised networks divide regions of certainty and regions of uncertainty.

104: Determine uncertainty corresponding to the original image according to the segmentation result set, the uncertainty being used for determining whether the original image is a to-be-labeled image. The uncertainty may also be referred to as labeling uncertainty, or automatic labeling uncertainty.

In this embodiment, the apparatus for determining a to-be-labeled image calculates uncertainty of the original image according to the segmentation result set. Whether the original image is suitable to be used as a to-be-labeled image may be determined based on the uncertainty. Generally, higher uncertainty indicates a higher probability that the original image is used as a to-be-labeled image. A lower uncertainty indicates that an automatic labeling (e.g., segmentation) of the original image is more likely to be accurate and there is lower chance that the image needs to be labeled manually by a professional staff, such as a doctor.

Figure 4:
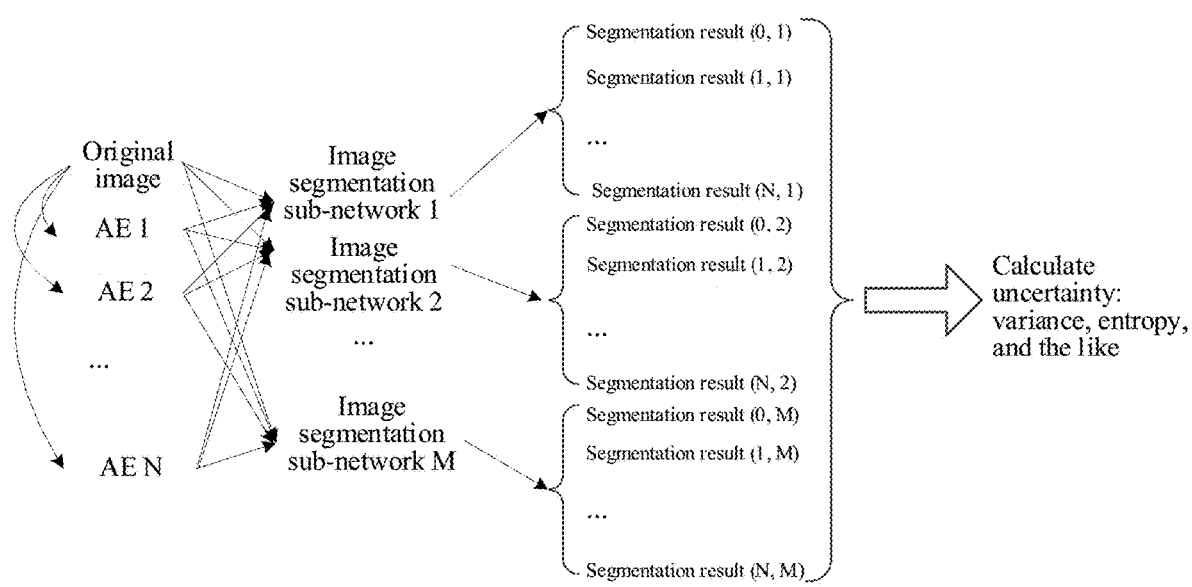
FIG. 4 is a schematic diagram of a network architecture of calculating uncertainty according to an embodiment of the present disclosure.

For ease of understanding, FIG. 4 is a schematic diagram of a network architecture used for calculating uncertainty according to an embodiment of the present disclosure. As shown in FIG. 4, it is assumed that there are N AEs, and the original image is separately inputted into different AEs, so as to obtain N encoded images; and then the N encoded images and the original image are respectively inputted into different image segmentation sub-networks, and there are M image segmentation sub-networks in total, so that [(N+1)*M] segmentation results are obtained; and finally, uncertainty of the original image is calculated based on the [(N+1)*M] segmentation results. The uncertainty may be a variance, an entropy, or another representation manner.

An embodiment of the present disclosure provides a method for determining a to-be-labeled image. First, an original image and an AE set are obtained, the original image being an image having not been labeled; then an encoded image set corresponding to the original image is obtained by using the AE set, the encoded image set including N encoded images, the encoded images being corresponding to the AEs; then the encoded image set and a segmentation result set corresponding to the original image are obtained by using an image segmentation network, the image segmentation network including M image segmentation sub-networks, and the segmentation result set including [(N+1)*M] segmentation results; and finally uncertainty corresponding to the original image is determined according to the segmentation result set, the uncertainty being used for determining whether the original image is a to-be-labeled image. By means of the foregoing method, the original image is changed by using AEs based on different encoding policies. Different AEs can focus on extracting information of the original image from different aspects, to differentiate the understanding of different AEs on the original image, so that some parts after the reconstruction are similar while the other parts vary in details. In addition, output results of different AEs are applied to different image segmentation sub-networks, which will make the output results more varied, so as to improve the calculation rationality of uncertainty, thereby helping to select more accurate to-be-labeled images.

In some embodiments, based on FIG. 3 and the embodiments corresponding to FIG. 3, in a first embodiment of the method for determining a to-be-labeled image provided in the embodiments of the present disclosure, the obtaining an encoded image set corresponding to the original image by using an AE set may include:

obtaining a first encoded image corresponding to the original image by using a first AE; and obtaining a second encoded image corresponding to the original image by using a second AE, the second AE and the first AE being two different types of AEs, and the second encoded image and the first encoded image being two different images.

In this embodiment, a method for generating encoded images based on a plurality of AEs is described. The apparatus for determining a to-be-labeled image may input the original image into the first AE for the first AE to output the first encoded image, and input the original image into the second AE for the second AE to output the second encoded image. It may be understood that, the first AE and the second AE are only an example, and in actual applications, there are a larger quantity and more types of AEs.

Specifically, types of the AEs include, but are not limited to: a sparse AE, a variational AE (VAE), a contractive AE (CAE), and a denoising AE (DAE), and a quantity of the AEs may be an integer greater than or equal to 1. The AE set in the present disclosure may include 10 AEs in total, which are two sparse AEs 1, two sparse AEs 2, two VAEs, two CAEs, and two DAEs.

The sparse AE may automatically learn features from unlabeled data, and provide a better feature description than that of original data. During actual applications, the original data may be replaced with the feature found by the spare AE, and this often leads to better results. The sparse AE 1 and the sparse AE 2 are two different types of sparse AEs.

The VAE is an important type of generation module, and compared with an AE, the VAE is more inclined to data generation. Provided that a decoder is trained well, the standard normally-distributed generated data can be used as an input of the decoder to generate new samples similar to but different from training data.

The CAE is only locally contracted, and an objective is to learn a manifold structure of data. A training objective function of the CAE is a sum of a reconstruction error and a contract penalty item (that is, a regularization item), and a learned representation $C(x)$ remains as constant as possible to an input x by minimizing the target function. A penalty item $\Omega(h)$ of the CAE is a squared Frobenius norm (sum of the squares of the elements) acting on a Jacobian matrix of the partial derivatives related to the function of the encoder. To put it simply, the penalty item is a sum of squares of elements of eigenvectors outputted by the encoder. The penalty term forces the model to learn a function whose objective does not change greatly as x changes little. Because the penalty is only applicable to the training data, it forces the AE learning to reflect features of distribution information of the training data.

The DAE can be trained by receiving an input with noise, and the core idea is that a neural network representation from which an original signal can be restored is not necessarily the best, and only a feature based on which "corrupted" original data can be encoded and decoded and then the real original data can be restored is a good feature.

Based on the foregoing description, before a backbone network, an input is changed by using AEs based on different policies. Different AEs can focus on extracting information of the image from different aspects, to differentiate the understanding of different AEs on the image, so that some parts after the reconstruction are similar while the other parts vary in details. Different AEs can also be added into different network structure units, which makes the AE more diversified and thus increases input uncertainty. Output results of different AEs are applied to different image segmentation sub-networks, so that output images are more varied and the uncertainty can be calculated more accurately.

Secondly, in this embodiment of the present disclosure, a method for generating encoded images based on a plurality of AEs is provided. That is, a first encoded image corresponding to an original image is obtained by using a first AE, and a second encoded image corresponding to the original image is obtained by a second AE. The second AE and the first AE are different types of AEs. By means of the foregoing method, a plurality of AEs can be used to encode an image. Because different AEs can focus on extracting different features of the image for encoding, different images generated by using the plurality of AEs vary little in a back bone position but vary greatly in details. Therefore, details of network understanding may be defined as "uncertainty", and this part is a region changed relatively greatly by the AE before and after, so that the segmentation results of the region with high uncertainty vary greatly during segmentation, so as to improve the reliability of uncertainty calculation.

In some embodiments, based on FIG. 3 and the embodiments corresponding to FIG. 3, in a second embodiment of the method for determining a to-be-labeled image provided in the embodiments of the present disclosure, the obtaining the encoded image set and a segmentation result set corresponding to the original image by using an image segmentation network may include:

obtaining a first segmentation result by using a first image segmentation sub-network, the first segmentation result including (N+1) first segmentation sub-results, the (N+1) first segmentation sub-results being corresponding to the encoded images in the encoded image set and the original image; and obtaining a second segmentation result by using a second image segmentation sub-network, the second segmentation result including (N+1) second segmentation sub-results, the (N+1) second segmentation sub-results being corresponding to the encoded images in the encoded image set and the original image, and the second image segmentation sub-network and the first image segmentation sub-network being two different types of image segmentation sub-networks.

In this embodiment, a method for generating segmentation results based on a plurality of image segmentation sub-networks is described. An apparatus for determining a to-be-labeled image may input N encoded images and an original image into a first image segmentation sub-network to obtain (N+1) first segmentation sub-results. For example, one encoded image corresponds to one first segmentation sub-result, and the original image corresponds to another first segmentation sub-result, and finally (N+1) first segmentation sub-results are obtained. The (N+1) first segmentation sub-results are the first segmentation result. Similarly, N encoded images and an original image are inputted into a second image segmentation sub-network to obtain (N+1) second segmentation sub-results. For example, one encoded image corresponds to one second segmentation sub-result, and the original image corresponds to another second segmentation sub-result, and finally (N+1) second segmentation sub-results are obtained. The (N+1) second segmentation sub-results are the second segmentation result.

It may be understood that, the first image segmentation sub-network and the second image segmentation sub-network are only an example, and in actual applications, there are a larger quantity and more types of image segmentation sub-networks. Specifically, a type of the image segmentation sub-network includes, but is not limited to, a U-Net and an FCN.

Figure 5:
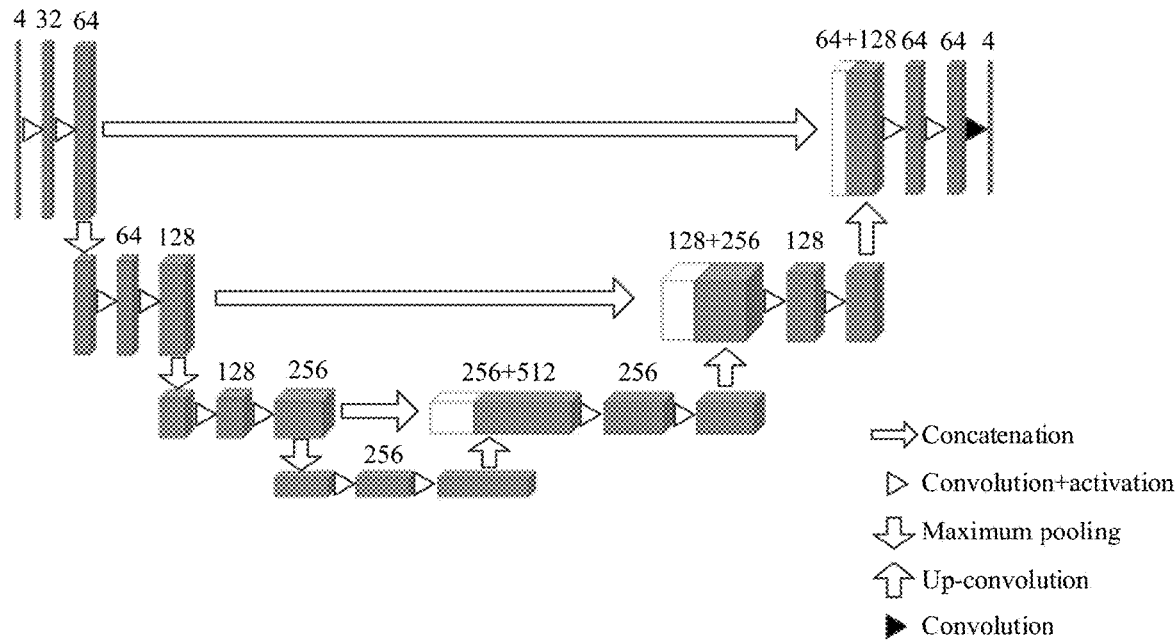
FIG. 5 is a schematic structural diagram of a U-Net according to an embodiment of the present disclosure.

For ease of description, FIG. 5 is a schematic structural diagram of a U-Net according to an embodiment of the present disclosure. As shown in FIG. 5, the U-Net is a deformation of a convolutional neural network. The whole neural network mainly includes two parts, namely a contraction path and an expansion path. The contraction path is mainly used for capturing context information of a picture. The expansion path symmetrical to contraction path is used for an accurate localization on a part that needs to be segmented in the picture. One of the main premises of the birth of the U-Net is that a structure of deep learning requires a large quantity of samples and computing resources in many cases. The U-Net is improved based on the FCN, and data enhancement may be used to train some data with a relatively small quantity of samples, especially medical data. This is because an acquisition cost of medical data is higher than that of pictures and other text data we have seen in general, both in terms of time and resource consumption. Therefore, the emergence of the U-Net is very helpful for deep learning to be used for medical images with a relatively small quantity of samples.

Figure 6:
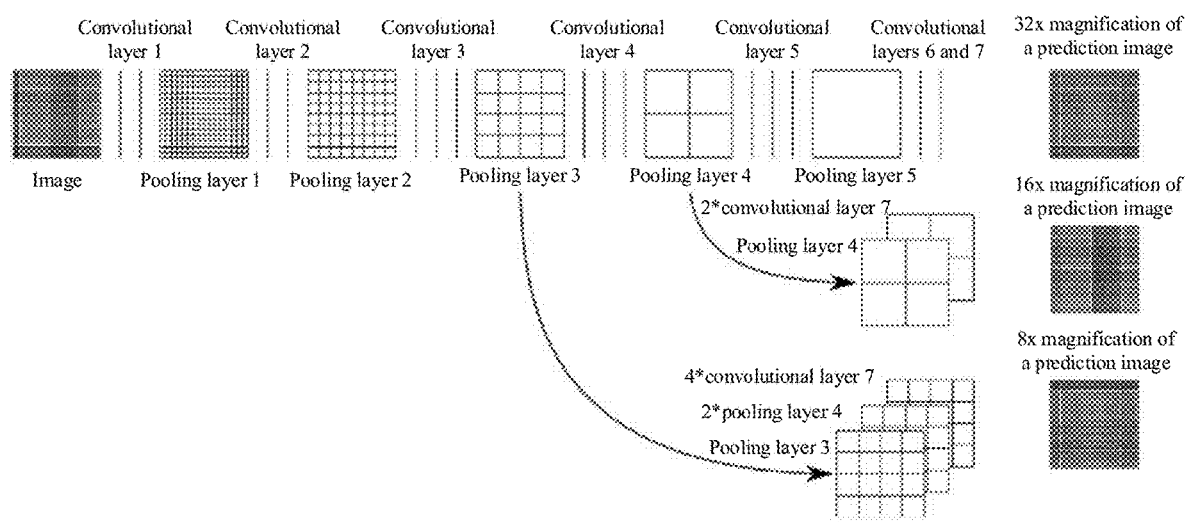
FIG. 6 is a schematic structural diagram of a fully convolutional network (FCN) according to an embodiment of the present disclosure.

FIG. 6 is a schematic structural diagram of an FCN according to an embodiment of the present disclosure. As shown in FIG. 6, the FCN converts fully connected layers in conventional convolutional neural networks (CNNs) into convolutional layers. FIG. 6 shows a process of convolution and deconvolution upsampling, that is, deconvolution of the output of the fifth layer (32× magnification) to the original image size. The results were not accurate enough, and some details cannot be restored. Therefore, deconvolution is sequentially performed on an output of the fourth layer and an output of the third layer, which respectively requires 16× upsampling and 8× upsampling.

Secondly, in this embodiment of the present disclosure, a method for generating segmentation results based on a plurality of image segmentation sub-networks is provided. That is, a first segmentation result is obtained by using a first image segmentation sub-network, and a second segmentation result is obtained by using a second image segmentation sub-network. The second image segmentation sub-network and the first image segmentation sub-network are different types of image segmentation sub-networks. By means of the foregoing method, a plurality of image segmentation sub-networks can be used to segment an image. Because different image segmentation sub-networks can focus on extracting different segmentation regions of the image, by applying output results of different AEs to different image segmentation sub-networks, output images are more varied and a result of the uncertainty is more accurate.

In some embodiments, based on FIG. 3 and the embodiments corresponding to FIG. 3, in a third embodiment of the method for determining a to-be-labeled image provided in the embodiments of the present disclosure, the determining uncertainty corresponding to the original image according to the segmentation result set may include:

obtaining a grayscale value corresponding to each pixel in the original image;

determining an entropy set corresponding to each pixel in the original image according to the segmentation result set and the grayscale value corresponding to each pixel in the original image, the entropy set including [(N+1)*M] entropies; and calculating the uncertainty corresponding to the original image according to the entropy set corresponding to each pixel in the original image.

In this embodiment, a manner of calculating uncertainty based on an entropy is provided, and uncertainty corresponding to an original image is calculated after [(N+1)*M] segmentation results are obtained. Specifically, it is assumed that N is 10 and M is 2, and (10+1)*2=22 segmentation results may be obtained. Uncertainty is calculated for the 22 segmentation results. The following manner may be specifically used for calculating:

$$H[x_i] = -\sum_{c=1}^{C} \frac{1}{T}\sum_{t=1}^{T} p(\hat{y}_t = c \mid x_i) * \log(p(\hat{y}_t = c \mid x_t));$$

where $H[x_i]$ represents an entropy corresponding to a grayscale value of an $i^{th}$ pixel, $x_i$ represents the grayscale value of the $i^{th}$ pixel in the original image, T represents a total quantity of segmentation results and may be 22 herein, t represents an integer greater than or equal to 1 and less than or equal to T, C represents a total quantity of network segmentation models and may be 2 herein, c represents an integer greater than or equal to 1 and less than or equal to C, and $\hat{y}_t$ represents a prediction probability of a $t^{th}$ segmentation result.

Therefore, the entropy set corresponding to each pixel in the original image is obtained, that is, an "entropy diagram" is obtained. It is assumed that each pixel has 22 results, the 22 results may be used to obtain a value of an entropy, which together makes a diagram. Then the entropies of all the pixels are averaged to obtain a value, that is, the uncertainty. Through experiments, a sequence of uncertainty of unlabeled data is used, and the top 20% of unlabeled data with relatively high uncertainty are labeled and trained together with the original labeled data. An obtained dice value is close to a result obtained through training after all the unlabeled data are labeled and trained together with the labeled data, which is much higher than a value obtained by randomly taking 20% of the unlabeled data to be labeled and trained together with the original labeled data.

Secondly, in this embodiment of the present disclosure, a manner of calculating uncertainty is provided. That is, a grayscale value corresponding to each pixel in an original image is obtained, and then an entropy set corresponding to each pixel in the original image is determined according to a segmentation result set and the grayscale value corresponding to each pixel in the original image, and finally uncertainty corresponding to the original image is calculated according to the entropy set corresponding to each pixel in the original image. By means of the foregoing method, a feasible implementation is provided for calculating uncertainty, thereby improving operability and reliability of the solution.

In some embodiments, based on FIG. 3 and the embodiments corresponding to FIG. 3, in a fourth embodiment of the method for determining a to-be-labeled image provided in the embodiments of the present disclosure, the determining uncertainty corresponding to the original image according to the segmentation result set may include:

obtaining a grayscale value corresponding to each pixel in each of the segmentation results;

determining a variance of each pixel based on the segmentation result set and according to the grayscale value corresponding to each pixel in the each segmentation result; and determining the uncertainty corresponding to the original image according to the variance of each pixel and a total quantity of pixels.

In this embodiment, a manner of calculating uncertainty based on a variance is provided, and uncertainty corresponding to an original image is calculated after [(N+1)*M] segmentation results are obtained. Specifically, it is assumed that N is 10 and M is 2, and (10+1)*2=22 segmentation results may be obtained. Uncertainty is calculated for the 22 segmentation results. The following manner may be specifically used for calculating:

$$AVG = \frac{1}{CT}\sum_{c=1}^{C}\sum_{t=1}^{T} p(\hat{y}_t = c \mid x_i);$$

$$DEV = \frac{1}{CT}\sum_{c=1}^{C}\sum_{t=1}^{T} (p(\hat{y}_t = c \mid x_i) - AVG)^2;$$

where AVG represents an average value, DEV represents a variance, $x_i$ represents a grayscale value of an $i^{th}$ pixel in an original image, T represents a total quantity of segmentation results and may be 22 herein, t represents an integer greater than or equal to 1 and less than or equal to T, C represents a total quantity of network segmentation models and may be 2 herein, c represents an integer greater than or equal to 1 and less than or equal to C, and $\hat{y}_t$ represents a prediction probability of a $t^{th}$ segmentation result.

That is, the variance is a variance obtained based on [(N+1)*M] segmentation results of each pixel, and the uncertainty is a sum of the variances of the entire image divided by a quantity of the pixels.

It may be understood that, the uncertainty may alternatively be calculated in a cross entropy manner in the present disclosure. This is not limited herein.

Secondly, in this embodiment of the present disclosure, another manner of calculating uncertainty is provided. That is, a grayscale value corresponding to each pixel in each segmentation result is obtained first, and then a variance of each pixel is determined based on a segmentation result set and according to the grayscale value corresponding to each pixel in each segmentation result, and finally uncertainty corresponding to the original image is determined according to the variance of each pixel and a total quantity of pixels. By means of the foregoing method, another feasible implementation is provided for calculating uncertainty, thereby improving operability, reliability, and flexibility of the solution.

In some embodiments, based on FIG. 3 and the embodiments corresponding to FIG. 3, in a fifth embodiment of the method for determining a to-be-labeled image provided in the embodiments of the present disclosure, after the determining uncertainty corresponding to the original image according to the segmentation result set, the method may further include:

determining whether the uncertainty is greater than or equal to an uncertainty threshold; and determining the original image as the to-be-labeled image when the uncertainty is greater than or equal to the uncertainty threshold.

In this embodiment, a manner in which an apparatus for determining a to-be-labeled image automatically selects a to-be-labeled image is described. After calculating uncertainty of an original image, the apparatus for determining a to-be-labeled image may determine whether the uncertainty is greater than or equal to an uncertainty threshold. The following four manners may be specifically adopted:

1. Fix an Uncertainty Threshold.

It is assumed that a value of the uncertainty is greater than or equal to 0 and less than or equal to 1, then an uncertainty threshold is preset within the range from 0 to 1, for example, the uncertainty threshold is 0.8. Then, after uncertainty of an original image is calculated, whether the uncertainty is greater than or equal to 0.8 is determined. If the uncertainty is greater than or equal to 0.8, it indicates that the original image is a to-be-labeled image that needs to be labeled. In this case, the apparatus for determining a to-be-labeled image may directly push the to-be-labeled image to a terminal device, so that a user may directly label the to-be-labeled image on the terminal device.

2. Fix a Percentage of Selected Data.

It is assumed that a value of the uncertainty is greater than or equal to 0 and less than or equal to 1, and in this case, an uncertainty threshold needs to be selected within the range from 0 to 1. A determination manner of the uncertainty threshold is that: it is assumed that there are 1000 predicted images in total, and uncertainty of the 1000 images is sorted in descending order, and then images with the highest 10% of uncertainty are selected as to-be-labeled images, that is, 100 images with the highest uncertainty are selected as to-be-labeled images. In this case, the apparatus for determining a to-be-labeled image may directly push the to-be-labeled images to a terminal device, so that a user may directly label the to-be-labeled images on the terminal device.

3. Fix an Amount of Selected Data.

It is assumed that a value of the uncertainty is greater than or equal to 0 and less than or equal to 1, and in this case, an uncertainty threshold needs to be selected within the range from 0 to 1. A determination manner of the uncertainty threshold is that: it is assumed that there are 1000 predicted images in total, and uncertainty of the 1000 images is sorted in descending order, and 50 images with the highest uncertainty are selected as to-be-labeled images. In this case, the apparatus for determining a to-be-labeled image may directly push the to-be-labeled images to a terminal device, so that a user may directly label the to-be-labeled images on the terminal device.

4. Float an Uncertainty Threshold.

It is assumed that a value of the uncertainty is greater than or equal to 0 and less than or equal to 1, and in this case, an uncertainty threshold needs to be selected within the range from 0 to 1. A determination manner of the uncertainty threshold is that: it is assumed that there are 1000 predicted images in total, and uncertainty of the 1000 images is sorted in descending order, and then first 100 images with the highest uncertainty are selected and an average value of uncertainty of the 100 images is calculated. It is assumed that an obtained value is 0.85, and 0.85 is determined as the uncertainty threshold. After uncertainty of an original image is calculated, whether the uncertainty is greater than or equal to 0.85 is determined. If the uncertainty is greater than or equal to 0.85, it indicates that the original image is a to-be-labeled image that needs to be labeled. In this case, the apparatus for determining a to-be-labeled image may directly push the to-be-labeled image to a terminal device, so that a user may directly label the to-be-labeled image on the terminal device.

Secondly, in this embodiment of the present disclosure, a method for automatically providing a to-be-labeled image based on uncertainty is provided. After uncertainty corresponding to an original image is determined according to a segmentation result set, whether the uncertainty is greater than or equal to an uncertainty threshold may be further determined, and if the uncertainty is greater than or equal to the uncertainty threshold, the original image is determined as a to-be-labeled image. By means of the foregoing method, whether the original image is suitable to be used as a to-be-labeled image can be automatically determined according to uncertainty. In this case, on the one hand, selection efficiency for a to-be-labeled image can be improved without the need to manually screen a to-be-labeled image according to uncertainty; on the other hand, selection accuracy for a to-be-labeled image can be effectively improved to prevent omission of selection of a to-be-labeled image.

In some embodiments, based on FIG. 3 and the embodiments corresponding to FIG. 3, in a sixth embodiment of the method for determining a to-be-labeled image provided in the embodiments of the present disclosure, before the obtaining an original image and an AE set, the method may further include:

obtaining a training image, the training image being an image having been labeled;

encoding the training image by using an encoder of a AE to be trained to obtain an encoded result;

decoding the encoded result by using a decoder of the AE to be trained to obtain a prediction image;

training the AE to be trained by using the training image and the prediction image until a loss function converges, to obtain an AE model parameter; and generating an AE according to the AE model parameter, the AE being one AE in the AE set.

Figure 7:
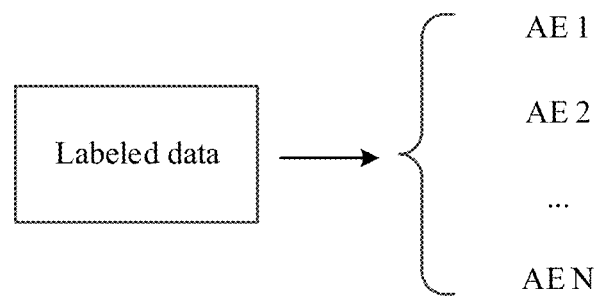
FIG. 7 is a schematic diagram of an embodiment of training an AE according to an embodiment of the present disclosure.

In this embodiment, a manner of training an AE is introduced. During training, labeled data needs to be used, that is, a training image needs to be trained. FIG. 7 is a schematic diagram of an embodiment of training an AE according to an embodiment of the present disclosure. As shown in FIG. 7, an AE 1 to an AE N may be respectively obtained by training a large quantity of training images. The training image may be a preprocessed image, for example, the training image is normalized. For a lesion area with no fixed shape, size, and direction, data augmentation operations such as flip, rotation, zooming, and contrast enhancement may be performed on the training image, so as to increase the quantity of training samples and increase the information value under different directions and sizes.

Figure 8:
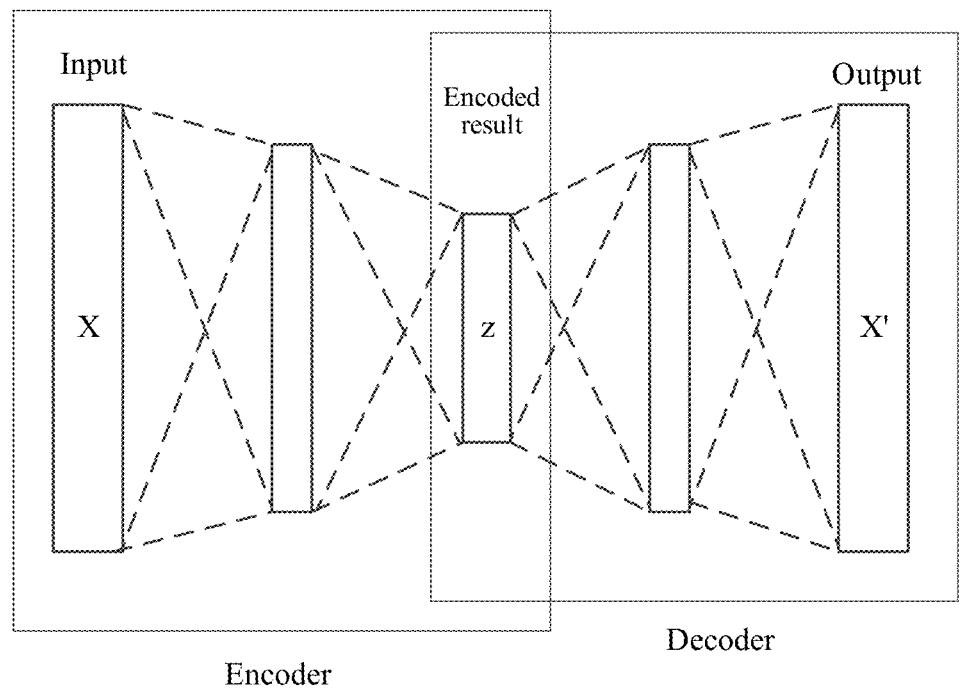
FIG. 8 is a schematic diagram of an AE according to an embodiment of the present disclosure.

FIG. 8 is a schematic diagram of an AE according to an embodiment of the present disclosure. As shown in FIG. 8, the AE includes two parts: an encoder and a decoder. The encoder is configured to compress an input into a potential spatial representation, and the decoder is configured to reconstruct an input from a potential spatial representation. An input of the encoder is represented as X, and an encoded result obtained through encoding is represented as z, that is, z=h(X). An input of the decoder is z, and an output of the decoder is X', that is, X'=y(z). According to the present disclosure, each AE needs to be trained. A prediction image is obtained after a training image is encoded and decoded by using a AE to be trained, and when a difference between the prediction image and the training image is small enough, a loss function converges. In this case, an AE model parameter of the encoder and the decoder is obtained, and a final AE is generated according to the AE model parameter.

Specifically, using a sparse AE 1 as an example, a KL divergence is $$\beta \sum_{j=1}^{S2} KL(\rho \| \hat{\rho}_j),$$

and a mean square error (MSE) is $$\sum_{i=1}^{n} (x_i - \hat{x}_i)^2,$$

where $\beta=3$, $\rho=0.2$, or $\rho=0.05$. A loss function may be $$L = \beta \sum_{j=1}^{S2} KL(\rho \| \hat{\rho}_j) + \sum_{i=1}^{n} (x_i - \hat{x}_i)^2.$$

Using a sparse AE 2 as an example, an L1 is $$\lambda \sum_{i} |a_i^{(h)}|,$$

an MSE is $$\sum_{i=1}^{n} (x_i - \hat{x}_i)^2,$$

where $\lambda=1$, L1=10e−3 or L1=10e−5. A loss function may be $$L = \lambda \sum_{i} |a_i^{(h)}| + \sum_{i=1}^{n} (x_i - \hat{x}_i)^2.$$

Using a VAE as an example, a KL divergence is $\lambda(1+\log \sigma^{-2} - u^2 - \exp(\log \sigma^{-2}))$, an MSE is $$\sum_{i=1}^{n}(x_i - \hat{x}_i)^2,$$

where $\lambda=0.5$ or $\lambda=0.2$. A loss function may be $$L = \lambda(1 + \log \sigma^2 - u^2 - \exp(\log \sigma^2)) + \sum_{i=1}^{n}(x_i - \hat{x}_i)^2.$$

Using a CAE as an example, an L2 is $$\lambda \sum_{i} \|\nabla x a_i^{(h)}(x)\|^2,$$

an MSE is $$\sum_{i=1}^{n}(x_i - \hat{x}_i)^2,$$

where $\lambda=1$, L2=10e−3 or L2=10e−5. A loss function is $$L = \lambda \sum_{i} \|\nabla x a_i^{(h)}(x)\|^2 + \sum_{i=1}^{n}(x_i - \hat{x}_i)^2.$$

Using a CAE as an example, an MSE is $$\sum_{i=1}^{n}(x_i - \hat{x}_i)^2,$$

and a Gaussian noise parameter Theta=0.5 or Theta=0.2. A loss function is $$L = \sum_{i=1}^{n}(x_i - \hat{x}_i)^2.$$

It may be understood that, the foregoing types of AEs are only an example, and is not to be understood as a limitation to the present disclosure. In addition, loss functions of the foregoing AEs are also only an example, and during actual applications, the loss functions may alternatively be flexibly adjusted as required.

Secondly, in this embodiment of the present disclosure, an AE training method is provided. That is, a training image is obtained first; then the training image is encoded by using an encoder of a AE to be trained to obtain an encoded result; then the encoded result is decoded by using a decoder of the AE to be trained to obtain a prediction image; and finally the AE to be trained is trained by using the training image and the prediction image until a loss function converges, to obtain an AE model parameter, and the AE is generated by using the AE model parameter. By means of the foregoing method, a feasible implementation is provided for training an AE, thereby improving feasibility and operability of the solution.

In some embodiments, based on FIG. 3 and the embodiments corresponding to FIG. 3, in a seventh embodiment of the method for determining a to-be-labeled image provided in the embodiments of the present disclosure, before the obtaining the encoded image set and a segmentation result set corresponding to the original image by using an image segmentation network, the method may further include:

obtaining a training image, the training image being an image having been labeled;

obtaining a prediction image corresponding to the training image by using an image segmentation sub-network;

training the image segmentation sub-network by using the training image and the prediction image until a loss function converges, to obtain a network model parameter; and generating an image segmentation sub-network according to the network model parameter, the image segmentation sub-network being one image segmentation sub-network in the image segmentation network.

Figure 9:
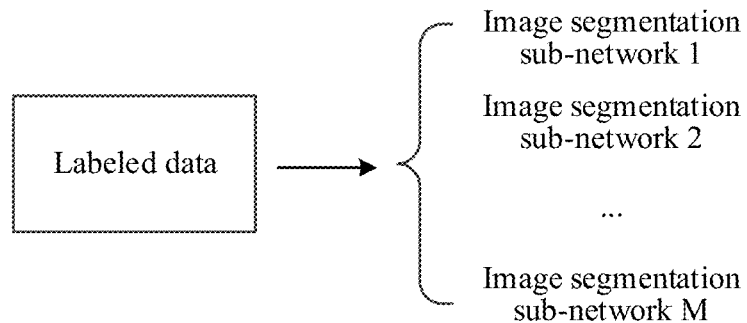
FIG. 9 is a schematic diagram of an embodiment of training an image segmentation sub-network according to an embodiment of the present disclosure.

In this embodiment, a manner of training an image segmentation sub-network is introduced. During training, labeled data needs to be used, that is, a training image needs to be trained. FIG. 9 is a schematic diagram of an embodiment of training an image segmentation sub-network according to an embodiment of the present disclosure. As shown in FIG. 9, an image segmentation sub-network 1 to an image segmentation sub-network M may be respectively obtained by training a large quantity of training images. The training image may be a preprocessed image, for example, the training image is normalized. For a lesion area with no fixed shape, size, and direction, data augmentation operations such as flip, rotation, zooming, and contrast enhancement may be performed on the training image, so as to increase the quantity of training samples and increase the information value under different directions and sizes.

Specifically, labeled training images are divided into a training set and a test set, and two image segmentation sub-networks may be trained by using a classic U-Net and a classic FCN respectively, a parameter of a network is updated based on an adaptive moment estimation (Adam) gradient descent method, an initial learning rate is 0.05, and in Adam, betas=(0.95, 0.9995). A probability value obtained by using the image segmentation sub-network is segmented as a probability image, and each pixel value is a probability from 0 to 1. A loss function is a dice value, and by minimizing the loss function, an error gradient may be calculated and a gradient of the network may be updated through back propagation. After the foregoing network training, a final prediction probability value is used to obtain a segmentation result.

Figure 10:
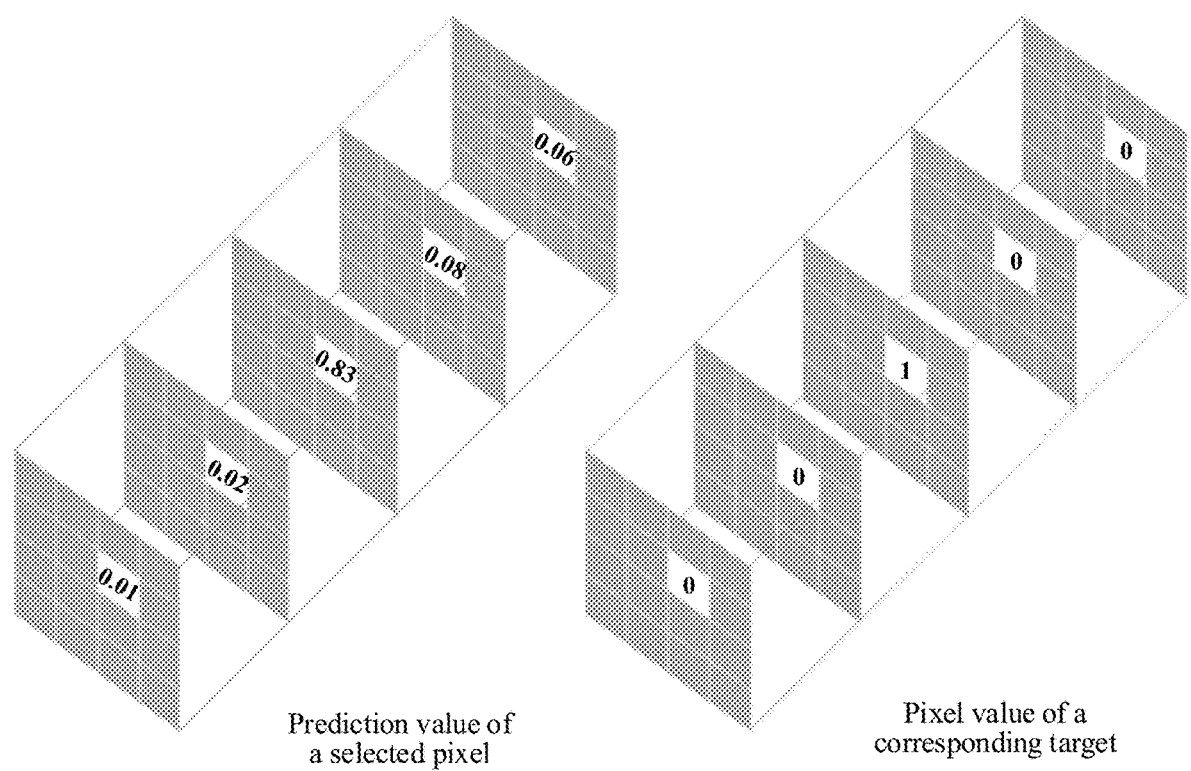
FIG. 10 is a schematic diagram based on an image segmentation sub-network according to an embodiment of the present disclosure.

The following describes an image segmentation sub-network training method based on a cross entropy. For ease of understanding, FIG. 10 is a schematic diagram of training an image segmentation sub-network according to an embodiment of the present disclosure. Specifically, a loss function most commonly used in image segmentation is a per-pixel cross entropy loss. The loss function examines each pixel separately and compares a category prediction (a pixel vector in a depth direction) with a hot-coded target vector. It is assumed that a pixel whose grayscale value is greater than 0.5 is recorded as 1, and a pixel whose grayscale value is less than or equal to 0.5 is recorded as 0. 0.83 is greater than 0.5, so that the pixel is recorded as 1. Grayscale values of other pixels are all less than 0.5, so that the pixels are all recorded as 0.

As can be seen, based on a loss function of the cross entropy, a category prediction of each pixel vector is individually evaluated, and then all the pixels are averaged. Therefore, it may be considered that pixels in the image are learned equally. However, categories are often unbalanced in medical images, which causes training to be dominated by categories of a relatively large quantity of pixels, and features of relatively small objects are difficult to be learned, and consequently, the effectiveness of the network is reduced.

The following describes an image segmentation sub-network training method based on a dice value. An overlapped part of two samples is measured by using a dice value. An indicator range is from 0 to 1, and "1" represents a complete overlap. To calculate a dice value of a predicted segmentation image, the overlap part is approximately a dot product between the prediction image and a label, and the elements in a result function are added.

Secondly, in this embodiment of the present disclosure, an image segmentation sub-network training method is provided. That is, a training image is obtained first; then a prediction image corresponding to the training image is obtained by using a image segmentation sub-network; then the image segmentation sub-network is trained by using the training image and the prediction image until a loss function converges, to obtain a network model parameter; and finally an image segmentation sub-network is generated according to the network model parameter. By means of the foregoing method, a feasible implementation is provided for training an AE, thereby improving feasibility and operability of the solution.

Figure 11:
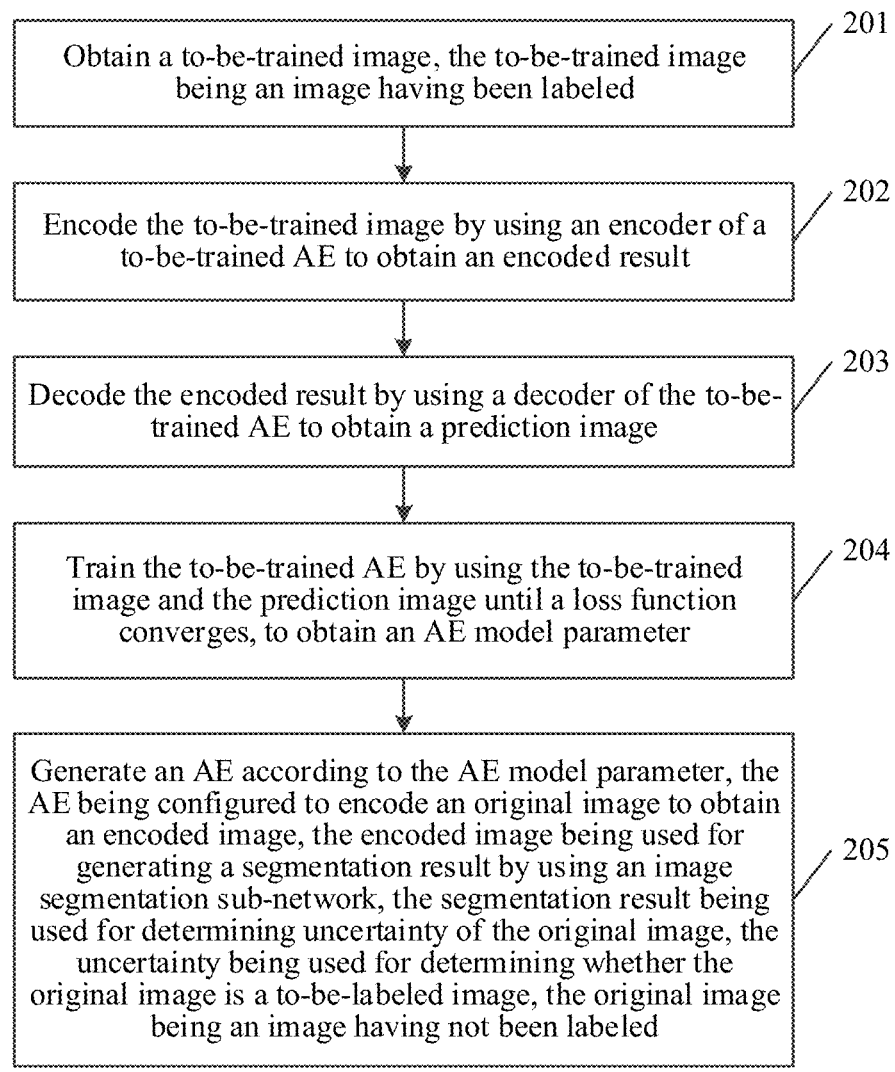
FIG. 11 is a schematic diagram of an embodiment of an AE training method according to an embodiment of the present disclosure.

The AE training method according to the present disclosure is described below based on the AE training manner and with reference to the foregoing descriptions. Referring to FIG. 11, an embodiment of the AE training method according to an embodiment of the present disclosure includes the following steps:

201: Obtain a training image, the training image being an image having been labeled.

In this embodiment, a model training apparatus obtains a training image. It may be understood that, the training image is an image having been labeled, and during training of an AE, a large quantity of training images are required for training. For ease of description, an example of training based on a training image is used for description. The model training apparatus is usually deployed on a server.

The training image may be a BraTS18 competition MR dataset including four modes, and the four modes are respectively T1, T2, TIC, and FLAIR. Certainly, in actual applications, other types of training images may alternatively be adopted. Then, the training image may be normalized. For a lesion area with no fixed shape, size, and direction, data augmentation operations such as flip, rotation, zooming, and contrast enhancement may be performed on the training image, so as to increase the quantity of training samples and increase the information value under different directions and sizes.

202: Encode the training image by using an encoder of a AE to be trained to obtain an encoded result.

In this embodiment, the model training apparatus inputs the training image into an encoder of a AE to be trained, and the encoder is configured to compress an input into a potential spatial representation. An encoded result is obtained after processing of the encoder of the AE to be trained.

203: Decode the encoded result by using a decoder of the AE to be trained to obtain a prediction image.

In this embodiment, the model training apparatus inputs the encoded result obtained through encoding into a decoder of the AE to be trained, and the decoder is configured to reconstruct an input from a potential spatial representation. A prediction image is obtained after processing of the decoder of the AE to be trained. It may be understood that, initial model parameters of the encoder and the decoder of the AE to be trained may be preset.

204: Train the AE to be trained by using the training image and the prediction image until a loss function converges, to obtain an AE model parameter.

In this embodiment, the model training apparatus performs calculation by using a loss function and based on the training image and the prediction image. Specifically, different types of AE to be trained usually adopt different loss functions, and reference may be made to the description of the foregoing embodiments, and details are not repeated herein. When the loss function converges, a corresponding AE model parameter is obtained.

205: Generate an AE according to the AE model parameter, the AE being configured to encode an original image to obtain an encoded image, the encoded image being used for generating a segmentation result by using an image segmentation sub-network, the segmentation result being used for determining uncertainty of the original image, the uncertainty being used for determining whether the original image is a to-be-labeled image, the original image being an image having not been labeled.

In this embodiment, according to the generated AE parameter, the model training apparatus uses the AE parameter as a model parameter of the AE, so as to obtain a final AE. Therefore, during prediction, the AE may be used to encode the original image.

It may be understood that, in actual applications, operations from step 201 to step 205 need to be performed on a plurality of AEs. Only an example of training one AE is used for description herein, however, it is not to be understood as a limitation to the present disclosure.

In this embodiment of the present disclosure, an AE training method is provided. That is, a training image is obtained first; then the training image is encoded by using an encoder of a AE to be trained to obtain an encoded result; then the encoded result is decoded by using a decoder of the AE to be trained to obtain a prediction image; and finally the AE to be trained is trained by using the training image and the prediction image until a loss function converges, to obtain an AE model parameter, and the AE is generated by using the AE model parameter. By means of the foregoing method, a feasible implementation is provided for training an AE, thereby improving feasibility and operability of the solution.

Figure 12:
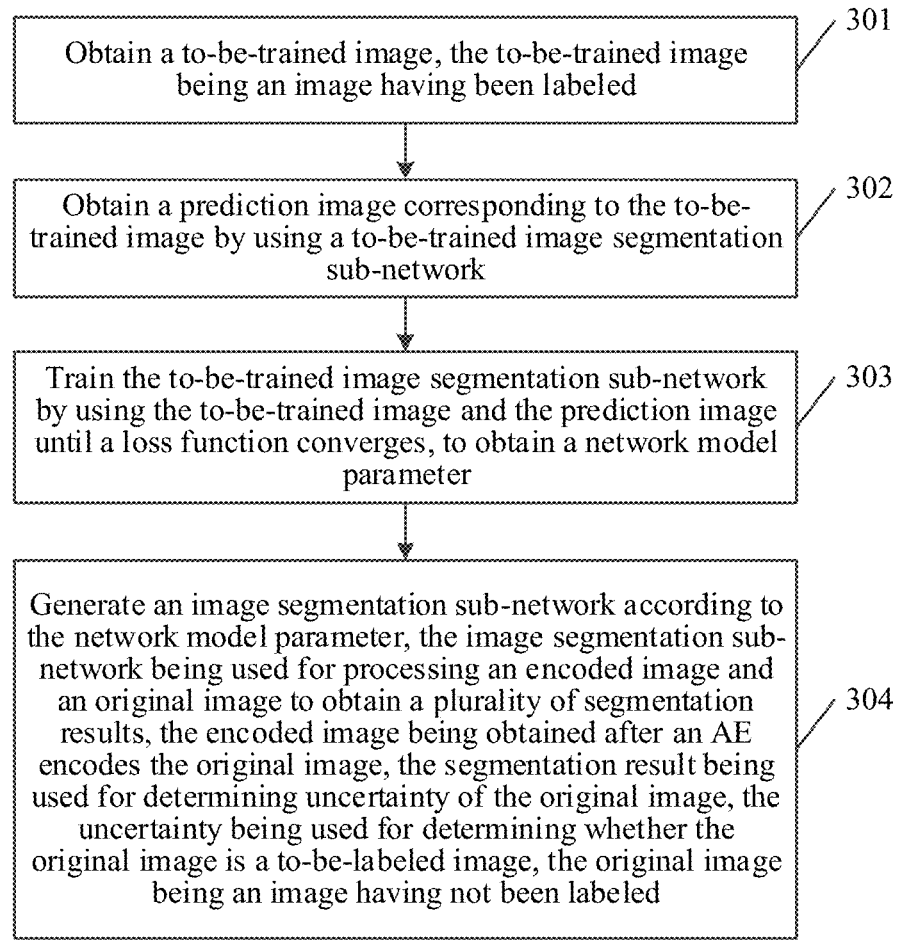
FIG. 12 is a schematic diagram of another embodiment of an image segmentation sub-network training method according to an embodiment of the present disclosure.

The image segmentation sub-network training method according to the present disclosure is described below based on an image segmentation sub-network training manner and with reference to the foregoing descriptions. Referring to FIG. 12, an embodiment of the image segmentation sub-network training method according to an embodiment of the present disclosure includes the following steps:

301: Obtain a training image, the training image being an image having been labeled.

In this embodiment, a model training apparatus obtains a training image. It may be understood that, the training image is an image having been labeled, and during training of an image segmentation sub-network, a large quantity of training images are required for training. For ease of description, an example of training an image segmentation sub-network based on a training image is used for description herein. The model training apparatus is usually deployed on a server.

The training image may be a BraTS18 competition MR dataset including four modes, and the four modes are respectively T1, T2, T1C, and FLAIR. Certainly, in actual applications, other types of training images may alternatively be adopted. Then, the training image needs to be normalized. For a lesion area with no fixed shape, size, and direction, data augmentation operations such as flip, rotation, zooming, and contrast enhancement may be performed on the training image, so as to increase the quantity of training samples and increase the information value under different directions and sizes.

302: Obtain a prediction image corresponding to the training image by using an image segmentation sub-network.

In this embodiment, the model training apparatus inputs the training image into the image segmentation sub-network, and the image segmentation sub-network is configured to segment the image, so as to obtain a segmented prediction image.

303: Train the image segmentation sub-network by using the training image and the prediction image until a loss function converges, to obtain a network model parameter.

In this embodiment, the model training apparatus performs calculation by using a loss function and based on the training image and the prediction image. Specifically, different loss functions may be adopted for different types of image segmentation sub-networks, or appropriate loss functions may be selected based on different types of segmentation models. When the loss function converges, a corresponding network model parameter is obtained.

304: Generate an image segmentation sub-network according to the network model parameter, the image segmentation sub-network being used for processing an encoded image and an original image to obtain a plurality of segmentation results, the encoded image being obtained after an AE encodes the original image, the segmentation result being used for determining uncertainty of the original image, the uncertainty being used for determining whether the original image is a to-be-labeled image, the original image being an image having not been labeled.

In this embodiment, according to the generated network model parameter, the model training apparatus uses the network model parameter as a model parameter of the image segmentation sub-network, so as to obtain a final image segmentation sub-network. Therefore, during prediction, the image segmentation sub-network may be used to segment the original image and the encoded image.

It may be understood that, in actual applications, operations from step 301 to step 304 need to be performed on a plurality of image segmentation sub-networks. Only an example of training one image segmentation sub-network is used for description herein, however, it is not to be understood as a limitation to the present disclosure.

In this embodiment of the present disclosure, an image segmentation sub-network training method is provided. That is, a training image is obtained first; then a prediction image corresponding to the training image is obtained by using a image segmentation sub-network; then the image segmentation sub-network is trained by using the training image and the prediction image until a loss function converges, to obtain a network model parameter; and finally an image segmentation sub-network is generated according to the network model parameter. By means of the foregoing method, a feasible implementation is provided for training an AE, thereby improving feasibility and operability of the solution.

Figure 13:
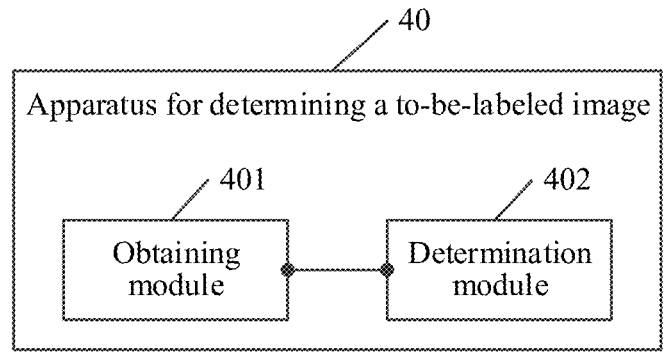
FIG. 13 is a schematic diagram of an embodiment of an apparatus for determining a to-be-labeled image according to an embodiment of the present disclosure.

An apparatus for determining a to-be-labeled image in the present disclosure is described below in detail. FIG. 13 is a schematic diagram of an embodiment of an apparatus for determining a to-be-labeled image according to an embodiment of the present disclosure, and the apparatus 40 for determining a to-be-labeled image includes:

an obtaining module 401, configured to obtain an original image and an AE set, the original image being an image having not been labeled, the AE set including N AEs, N being an integer greater than or equal to 1, the obtaining module 401 being further configured to obtain an encoded image set corresponding to the original image by using the AE set, the encoded image set including N encoded images, the encoded images being corresponding to the AEs, the obtaining module 401 being further configured to obtain the encoded image set and a segmentation result set corresponding to the original image by using an image segmentation network, the image segmentation network including M image segmentation sub-networks, and the segmentation result set including [(N+1)*M] segmentation results, M being an integer greater than or equal to 1; and a determination module 402, configured to determine uncertainty corresponding to the original image according to the segmentation result set obtained by the obtaining module 401, the uncertainty being used for determining whether the original image is a to-be-labeled image.

An embodiment of the present disclosure provides an apparatus for determining a to-be-labeled image. First, an original image and an AE set are obtained, the original image being an image having not been labeled; then an encoded image set corresponding to the original image is obtained by using the AE set, the encoded image set including N encoded images, the encoded images being corresponding to the AEs; then the encoded image set and a segmentation result set corresponding to the original image are obtained by using an image segmentation network, the image segmentation network including M image segmentation sub-networks, and the segmentation result set including [(N+1)*M] segmentation results; and finally uncertainty corresponding to the original image is determined according to the segmentation result set, the uncertainty being used for determining whether the original image is a to-be-labeled image. By means of the foregoing method, the original image is changed by using AEs based on different encoding policies. Different AEs can focus on extracting information of the original image from different aspects, to differentiate the understanding of different AEs on the original image, so that some parts after the reconstruction are similar while the other parts vary in details. In addition, output results of different AEs are applied to different image segmentation sub-networks, which will make the output results more varied, so as to improve the calculation rationality of uncertainty, thereby helping to select more accurate to-be-labeled images.

In some embodiments, based on the embodiment corresponding to FIG. 13, in another embodiment of the apparatus 40 for determining a to-be-labeled image provided in this embodiment of the present disclosure, the obtaining module 401 is specifically configured to:
obtain a first encoded image corresponding to the original image by using a first AE; and
obtain a second encoded image corresponding to the original image by using a second AE, the second AE and the first AE being two different types of AEs, and the second encoded image and the first encoded image being two different images.

Secondly, in this embodiment of the present disclosure, a manner of generating an encoded image based on a plurality of AEs is provided. That is, a first encoded image corresponding to an original image is obtained by using a first AE, and a second encoded image corresponding to the original image is obtained by a second AE. The second AE and the first AE are different types of AEs. By means of the foregoing method, a plurality of AEs can be used to encode an image. Because different AEs can focus on extracting different features of the image for encoding, different images generated by using the plurality of AEs vary little in a back bone position but vary greatly in details. Therefore, details of network understanding may be defined as "uncertainty", and this part is a region changed relatively greatly by the AE before and after, so that the segmentation results of the region with high uncertainty vary greatly during segmentation, so as to improve the reliability of uncertainty calculation.

In some embodiments, based on the embodiment corresponding to FIG. 13, in another embodiment of the apparatus 40 for determining a to-be-labeled image provided in this embodiment of the present disclosure,
the obtaining module 401 is specifically configured to:
obtain a first segmentation result by using a first image segmentation sub-network, the first segmentation result including (N+1) first segmentation sub-results, the (N+1) first segmentation sub-results being corresponding to the encoded images in the encoded image set and the original image; and
obtain a second segmentation result by using a second image segmentation sub-network, the second segmentation result including (N+1) second segmentation sub-results, the (N+1) second segmentation sub-results being corresponding to the encoded images in the encoded image set and the original image, and the second image segmentation sub-network and the first image segmentation sub-network being two different types of image segmentation sub-networks.

Secondly, in this embodiment of the present disclosure, a manner of generating a segmentation results based on a plurality of image segmentation sub-networks is provided. That is, a first segmentation result is obtained by using a first image segmentation sub-network, and a second segmentation result is obtained by using a second image segmentation sub-network. The second image segmentation sub-network and the first image segmentation sub-network are different types of image segmentation sub-networks. By means of the foregoing method, a plurality of image segmentation sub-networks can be used to segment an image. Because different image segmentation sub-networks can focus on extracting different segmentation regions of the image, by applying output results of different AEs to different image segmentation sub-networks, output images are more varied and a result of the uncertainty can be more accurate.

In some embodiments, based on the embodiment corresponding to FIG. 13, in another embodiment of the apparatus 40 for determining a to-be-labeled image provided in this embodiment of the present disclosure, the determination module 402 is specifically configured to: obtain a grayscale value corresponding to each pixel in the original image;
determine an entropy set corresponding to each pixel in the original image according to the segmentation result set and the grayscale value corresponding to each pixel in the original image, the entropy set including [(N+1)*M] entropies; and
calculate the uncertainty corresponding to the original image according to the entropy set corresponding to each pixel in the original image.

Secondly, in this embodiment of the present disclosure, a manner of calculating uncertainty is provided. That is, a grayscale value corresponding to each pixel in an original image is obtained, and then an entropy set corresponding to each pixel in the original image is determined according to a segmentation result set and the grayscale value corresponding to each pixel in the original image, and finally uncertainty corresponding to the original image is calculated according to the entropy set corresponding to each pixel in the original image. By means of the foregoing method, a feasible implementation is provided for calculating uncertainty, thereby improving operability and reliability of the solution.

In some embodiments, based on the embodiment corresponding to FIG. 13, in another embodiment of the apparatus 40 for determining a to-be-labeled image provided in this embodiment of the present disclosure,
the determination module 402 is specifically configured to: obtain a grayscale value corresponding to each pixel in each of the segmentation results;
determine a variance of each pixel based on the segmentation result set and according to the grayscale value corresponding to each pixel in the each segmentation result; and
determine the uncertainty corresponding to the original image according to the variance of each pixel and a total quantity of pixels.

Secondly, in this embodiment of the present disclosure, another manner of calculating uncertainty is provided. That is, a grayscale value corresponding to each pixel in each segmentation result is obtained first, and then a variance of each pixel is determined based on a segmentation result set and according to the grayscale value corresponding to each pixel in the each segmentation result, and finally uncertainty corresponding to the original image is determined according to the variance of each pixel and a total quantity of pixels. By means of the foregoing method, another feasible implementation is provided for calculating uncertainty, thereby improving operability, reliability, and flexibility of the solution.

Figure 14:
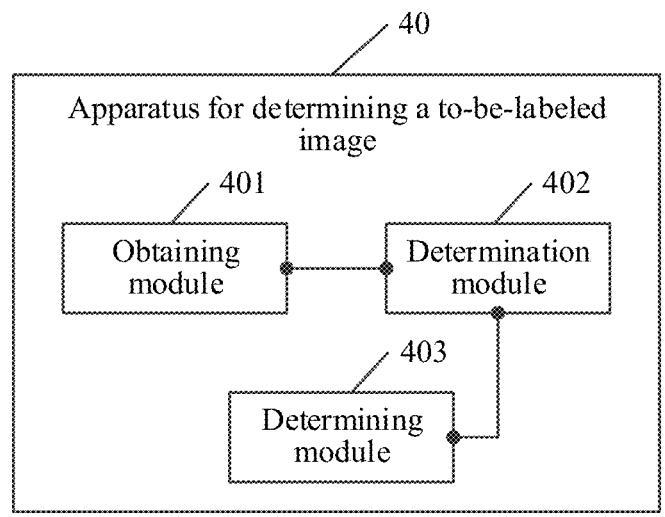
FIG. 14 is a schematic diagram of another embodiment of an apparatus for determining a to-be-labeled image according to an embodiment of the present disclosure.

In some embodiments, based on the embodiment corresponding to FIG. 13, referring to FIG. 14, in another embodiment of the apparatus 40 for determining a to-be-labeled image provided in this embodiment of the present disclosure, the apparatus 40 for determining a to-be-labeled image further includes a determining module 403.

The determining module 403 is configured to determine, after the determination module 402 determines the uncertainty corresponding to the original image according to the segmentation result set, whether the uncertainty is greater than or equal to an uncertainty threshold.

The determination module 402 is further configured to determine the original image as the to-be-labeled image when the determining module 403 determines that the uncertainty is greater than or equal to the uncertainty threshold.

Secondly, in this embodiment of the present disclosure, a manner of automatically providing a to-be-labeled image based on uncertainty is provided. After uncertainty corresponding to an original image is determined according to a segmentation result set, whether the uncertainty is greater than or equal to an uncertainty threshold may be further determined, and if the uncertainty is greater than or equal to the uncertainty threshold, the original image is determined as a to-be-labeled image. By means of the foregoing method, whether the original image is suitable to be used as a to-be-labeled image can be automatically determined according to uncertainty. In this case, on the one hand, selection efficiency for a to-be-labeled image can be improved without the need to manually screen a to-be-labeled image according to uncertainty; on the other hand, selection accuracy for a to-be-labeled image can be effectively improved to prevent omission of selection of a to-be-labeled image.

Figure 15:
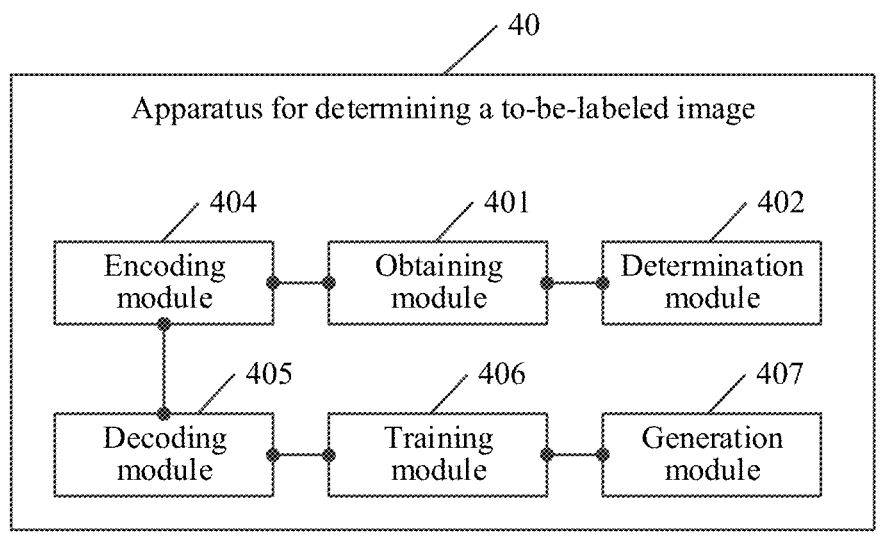
FIG. 15 is a schematic diagram of another embodiment of an apparatus for determining a to-be-labeled image according to an embodiment of the present disclosure.

In some embodiments, based on the embodiment corresponding to FIG. 13, referring to FIG. 15, in another embodiment of the apparatus 40 for determining a to-be-labeled image provided in this embodiment of the present disclosure, the apparatus for determining a to-be-labeled image further includes an encoding module 404, a decoding module 405, a training module 406, and a generation module 407.

The obtaining module 401 is further configured to obtain a training image before obtaining the original image and the AE set, the training image being an image having been labeled.

The encoding module 404 is configured to encode, by using an encoder of a AE to be trained, the training image obtained by the obtaining module 401 to obtain an encoded result.

The decoding module 405 is configured to decode, by using a decoder of the AE to be trained, the encoded result encoded by the encoding module 404 to obtain a prediction image.

The training module 406 is configured to train the AE to be trained by using the training image and the prediction image decoded by the decoding module 405 until a loss function converges, to obtain an AE model parameter.

The generation module 407 is configured to generate an AE according to the AE model parameter obtained through training by the training module 406, the AE being one AE in the AE set.

Secondly, in this embodiment of the present disclosure, an AE training manner is provided. That is, a training image is obtained first; then the training image is encoded by using an encoder of a AE to be trained to obtain an encoded result; then the encoded result is decoded by using a decoder of the AE to be trained to obtain a prediction image; and finally the AE to be trained is trained by using the training image and the prediction image until a loss function converges, to obtain an AE model parameter, and the AE is generated by using the AE model parameter. By means of the foregoing method, a feasible implementation is provided for training an AE, thereby improving feasibility and operability of the solution.

Figure 16:
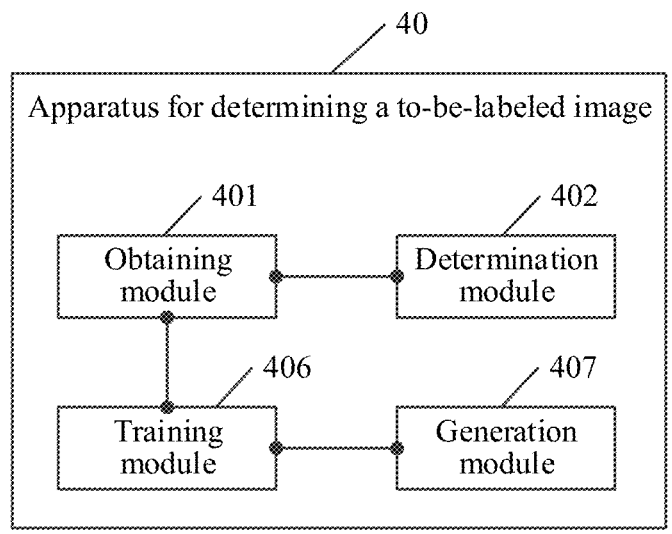
FIG. 16 is a schematic diagram of another embodiment of an apparatus for determining a to-be-labeled image according to an embodiment of the present disclosure.

In some embodiments, based on the embodiment corresponding to FIG. 13, referring to FIG. 16, in another embodiment of the apparatus 40 for determining a to-be-labeled image provided in this embodiment of the present disclosure, the apparatus 40 for determining a to-be-labeled image further includes a training module 406 and a generation module 407.

The obtaining module 401 is further configured to obtain a training image before obtaining the encoded image set and the segmentation result set corresponding to the original image by using the image segmentation network, the training image being an image having been labeled.

The obtaining module 401 is further configured to obtain a prediction image corresponding to the training image by using an image segmentation sub-network.

The training module 406 is configured to train the image segmentation sub-network by using the training image and the prediction image obtained by the obtaining module 401 until a loss function converges, to obtain a network model parameter.

The generation module 407 is configured to generate an image segmentation sub-network according to the network model parameter obtained through training by the training module 406, the image segmentation sub-network being one image segmentation sub-network in the image segmentation network.

Secondly, in this embodiment of the present disclosure, an image segmentation sub-network training manner is provided. That is, a training image is obtained first; then a prediction image corresponding to the training image is obtained by using a image segmentation sub-network; then the image segmentation sub-network is trained by using the training image and the prediction image until a loss function converges, to obtain a network model parameter; and finally an image segmentation sub-network is generated according to the network model parameter. By means of the foregoing method, a feasible implementation is provided for training an AE, thereby improving feasibility and operability of the solution.

Figure 17:
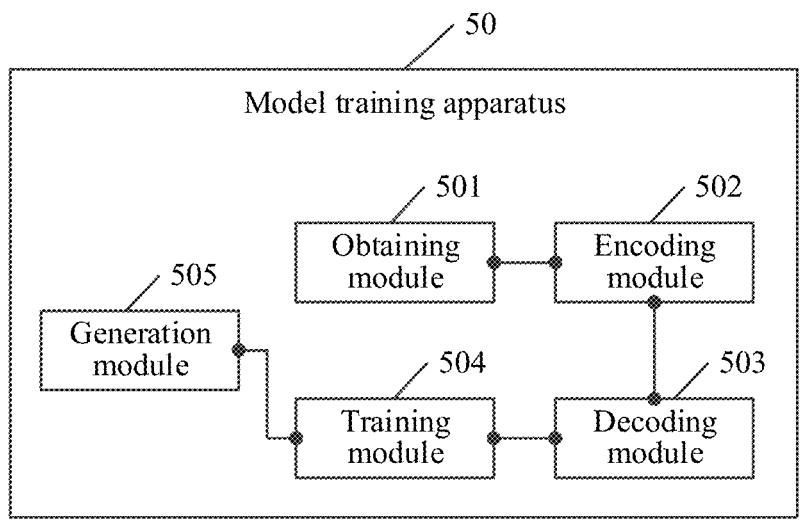
FIG. 17 is a schematic diagram of an embodiment of an AE training apparatus according to an embodiment of the present disclosure.

An AE training apparatus in the present disclosure is described below in detail. FIG. 17 is a schematic diagram of an embodiment of an AE training apparatus according to an embodiment of the present disclosure. The AE training apparatus 50 includes:

an obtaining module 501, configured to obtain a training image, the training image being an image having been labeled;

an encoding module 502, configured to encode, by using an encoder of a AE to be trained, the training image obtained by the obtaining module 501 to obtain an encoded result;

a decoding module 503, configured to decode, by using a decoder of the AE to be trained, the encoded result encoded by the encoding module 502 to obtain a prediction image;

a training module 504, configured to train the AE to be trained by using the training image and the prediction image decoded by the decoding module 503 until a loss function converges, to obtain an AE model parameter; and a generation module 505, configured to generate an AE according to the AE model parameter obtained through training by the training module 504, the AE being configured to encode an original image to obtain an encoded image, the encoded image being used for generating a segmentation result by using an image segmentation sub-network, the segmentation result being used for determining uncertainty of the original image, the uncertainty being used for determining whether the original image is a to-be-labeled image, the original image being an image having not been labeled.

In this embodiment of the present disclosure, an AE training apparatus is provided. That is, a training image is obtained first; then the training image is encoded by using an encoder of a AE to be trained to obtain an encoded result; then the encoded result is decoded by using a decoder of the AE to be trained to obtain a prediction image; and finally the AE to be trained is trained by using the training image and the prediction image until a loss function converges, to obtain an AE model parameter, and the AE is generated by using the AE model parameter. By means of the foregoing method, a feasible implementation is provided for training an AE, thereby improving feasibility and operability of the solution.

Figure 18:
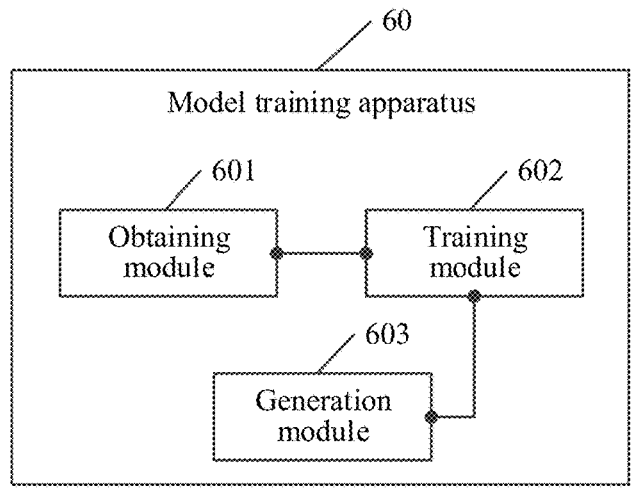
FIG. 18 is a schematic diagram of another embodiment of an image segmentation sub-network training apparatus according to an embodiment of the present disclosure.

An image segmentation sub-network training apparatus in the present disclosure is described below in detail. FIG. 18 is a schematic diagram of an embodiment of an image segmentation sub-network training apparatus according to an embodiment of the present disclosure. The image segmentation sub-network training apparatus 60 includes:

an obtaining module 601, configured to obtain a training image, the training image being an image having been labeled, the obtaining module 601 being further configured to obtain a prediction image corresponding to the training image by using an image segmentation sub-network;

a training module 602, configured to train the image segmentation sub-network by using the training image and the prediction image obtained by the obtaining module 601 until a loss function converges, to obtain a network model parameter; and a generation module 603, configured to generate an image segmentation sub-network according to the network model parameter obtained through training by the training module 602, the image segmentation sub-network being used for processing an encoded image and an original image to obtain a plurality of segmentation results, the encoded image being obtained after an AE encodes the original image, the segmentation result being used for determining uncertainty of the original image, the uncertainty being used for determining whether the original image is a to-be-labeled image, the original image being an image having not been labeled.

In this embodiment of the present disclosure, an image segmentation sub-network training apparatus is provided. That is, a training image is obtained first; then a prediction image corresponding to the training image is obtained by using a image segmentation sub-network; then the image segmentation sub-network is trained by using the training image and the prediction image until a loss function converges, to obtain a network model parameter; and finally an image segmentation sub-network is generated according to the network model parameter. By means of the foregoing method, a feasible implementation is provided for training an AE, thereby improving feasibility and operability of the solution.

The term unit (and other similar terms such as subunit, module, submodule, etc.) in this disclosure may refer to a software unit, a hardware unit, or a combination thereof. A software unit (e.g., computer program) may be developed using a computer programming language. A hardware unit may be implemented using processing circuitry and/or memory. Each unit can be implemented using one or more processors (or processors and memory). Likewise, a processor (or processors and memory) can be used to implement one or more units. Moreover, each unit can be part of an overall unit that includes the functionalities of the unit.

Figure 19:
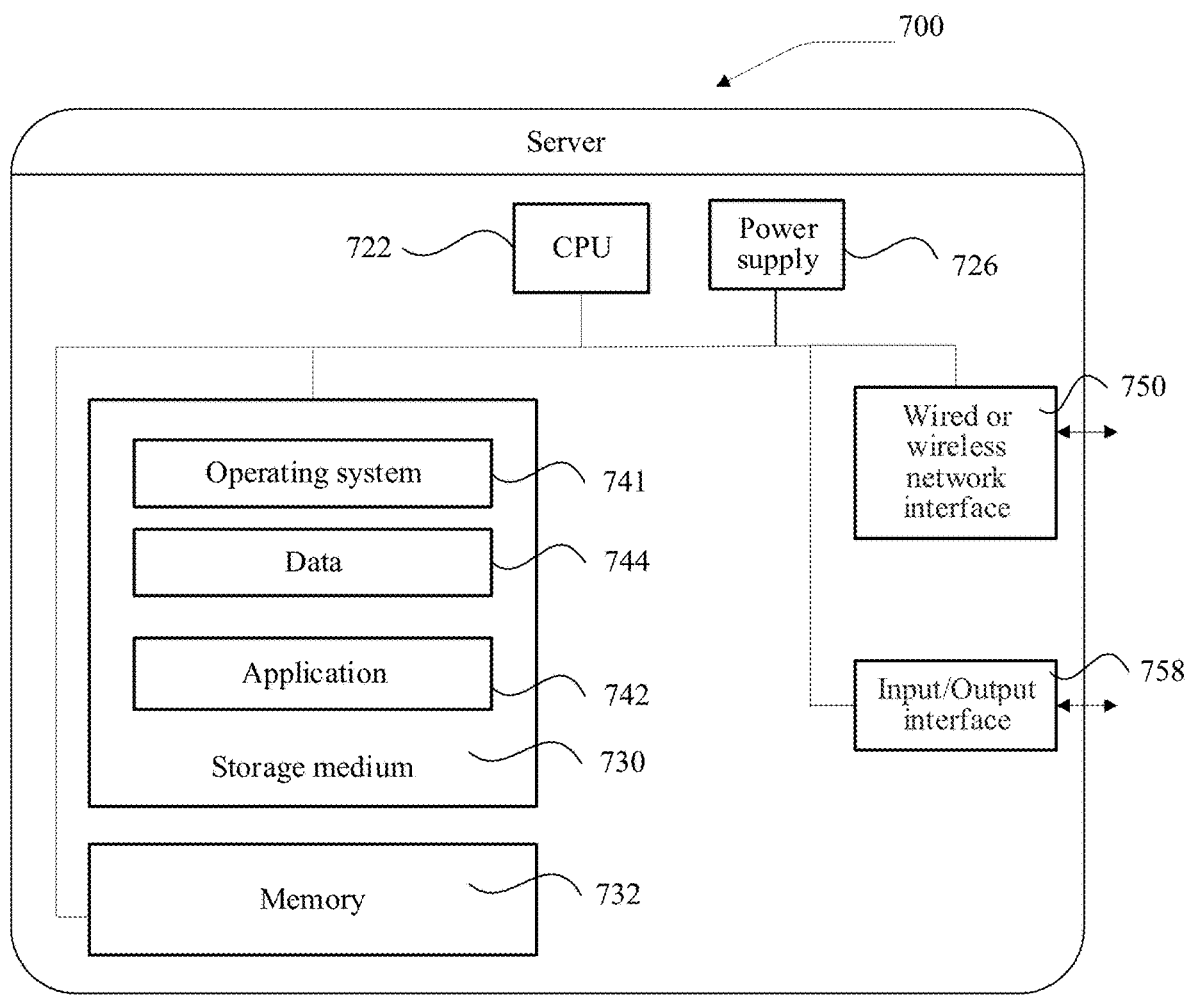
FIG. 19 is a schematic structural diagram of a server according to an embodiment of the present disclosure.

FIG. 19 is a schematic structural diagram of a server according to an embodiment of the present disclosure. The server 700 may vary greatly due to different configurations or performance, and may include one or more central processing units (CPUs) 722 (for example, one or more processors) and a memory 732, and one or more storage media 730 (for example, one or more mass storage devices) that store applications 742 or data 744. The memory 732 and the storage medium 730 may be transient storage or persistent storage. The program stored in the storage medium 730 may include one or more modules (not marked in the figure), and each module may include a series of instruction operations to the server. Still further, the CPU 722 may be configured to communicate with the storage medium 730 to perform the series of instruction operations in the storage medium 730 on the server 700.

The server 700 may further include one or more power supplies 726, one or more wired or wireless network interfaces 750, one or more input/output interfaces 758, and/or one or more operating systems 741, for example, Windows Server, Mac OS X™, Unix™, Linux, or FreeBSD™.

The steps performed by the server in the foregoing embodiment may be based on the structure of the server shown in FIG. 19.

In this embodiment of the present disclosure, the CPU 722 included in the server further has the following functions:

obtaining an original image and an AE set, the original image being an image having not been labeled, the AE set including N AEs, N being an integer greater than or equal to 1;

obtaining an encoded image set corresponding to the original image by using the AE set, the encoded image set including N encoded images, the encoded images being corresponding to the AEs;

obtaining the encoded image set and a segmentation result set corresponding to the original image by using an image segmentation network, the image segmentation network including M image segmentation sub-networks, and the segmentation result set including [(N+1)*M] segmentation results, M being an integer greater than or equal to 1; and determining uncertainty corresponding to the original image according to the segmentation result set, the uncertainty being used for determining whether the original image is a to-be-labeled image.

In this embodiment of the present disclosure, the CPU 722 included in the server further has the following functions:

obtaining a training image, the training image being an image having been labeled;

encoding the training image by using an encoder of a AE to be trained to obtain an encoded result;

decoding the encoded result by using a decoder of the AE to be trained to obtain a prediction image;

training the AE to be trained by using the training image and the prediction image until a loss function converges, to obtain an AE model parameter; and generating an AE according to the AE model parameter, the AE being configured to encode an original image to obtain an encoded image, the encoded image being used for generating a segmentation result by using an image segmentation sub-network, the segmentation result being used for determining uncertainty of the original image, the uncertainty being used for determining whether the original image is a to-be-labeled image, the original image being an image having not been labeled.

In this embodiment of the present disclosure, the CPU 722 included in the server further has the following functions:

obtaining a training image, the training image being an image having been labeled;

obtaining a prediction image corresponding to the training image by using an image segmentation sub-network;

training the image segmentation sub-network by using the training image and the prediction image until a loss function converges, to obtain a network model parameter; and generating an image segmentation sub-network according to the network model parameter, the image segmentation sub-network being used for processing an encoded image and an original image to obtain a plurality of segmentation results, the encoded image being obtained after an AE encodes the original image, the segmentation result being used for determining uncertainty of the original image, the uncertainty being used for determining whether the original image is a to-be-labeled image, the original image being an image having not been labeled.

Figure 20:
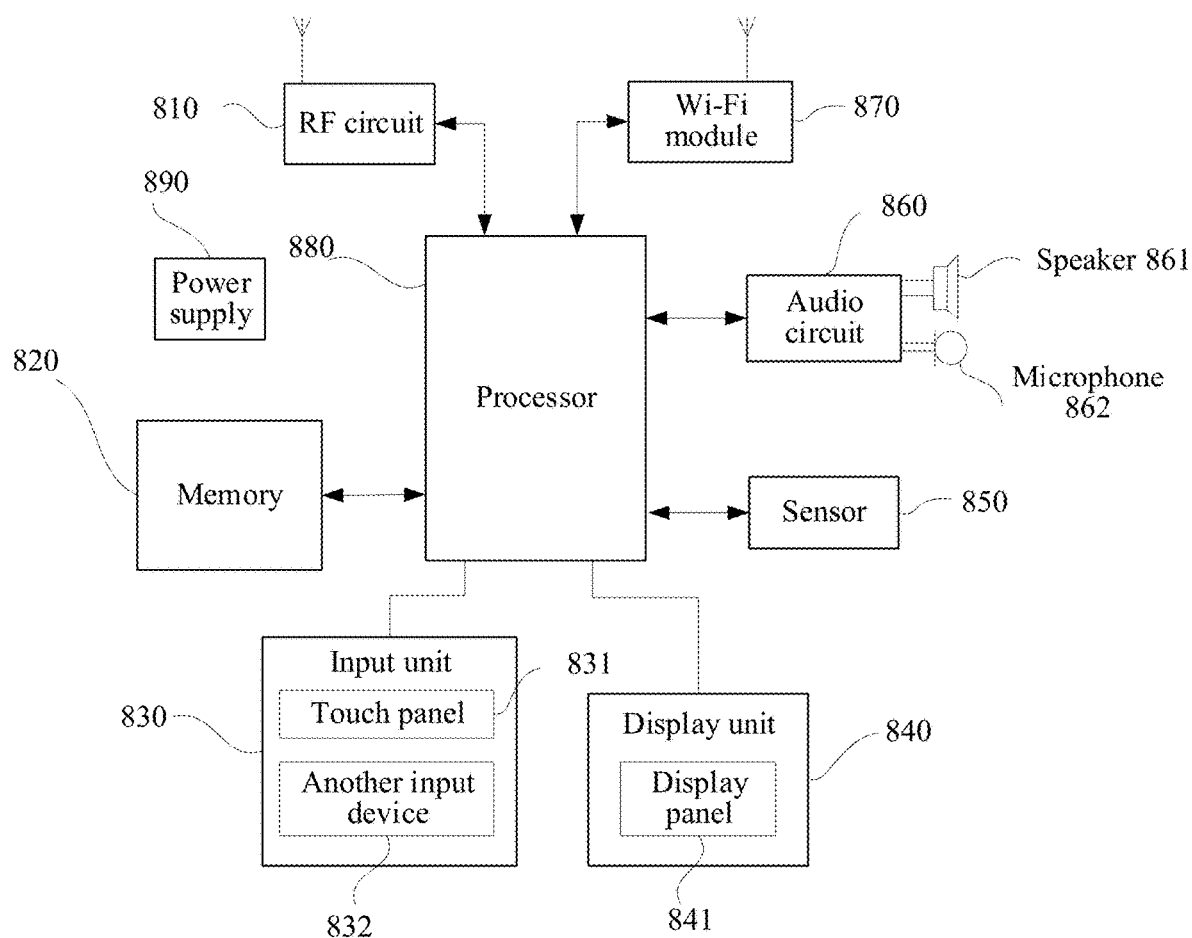
FIG. 20 is a schematic structural diagram of a terminal device according to an embodiment of the present disclosure.

An embodiment of the present disclosure further provides another apparatus for determining a to-be-labeled image, as shown in FIG. 20. For ease of description, only parts related to this embodiment of the present disclosure are shown. For specific technical details that are not disclosed, refer to the method part of the embodiments of the present disclosure. The terminal device may be any terminal device including a mobile phone, a tablet computer, a personal digital assistant (PDA), a point of sales (POS), and an on-board computer, and the terminal device being a mobile phone is used as an example.

FIG. 20 shows a block diagram of the structure of a part of the mobile phone related to the terminal device according to this embodiment of the present disclosure. Referring to FIG. 20, the mobile phone includes components such as: a radio frequency (RF) circuit 810, a memory 820, an input unit 830, a display unit 840, a sensor 850, an audio circuit 860, a wireless fidelity (Wi-Fi) module 870, a processor 880, and a power supply 890. A person skilled in the art can understand that the structure of the mobile phone shown in FIG. 20 does not constitute a limitation to the mobile phone, and the mobile phone may include more components or fewer components than those shown in the figure, or some components may be combined, or a different component deployment may be used.

The following makes a detailed description of the components of the mobile phone with reference to FIG. 20.

The RF circuit 810 may be configured to receive and transmit a signal in an information receiving and transmitting process or a call process, and in particular, after receiving downlink information of a base station, transmit the downlink information to the processor 880 for processing. In addition, the RF circuit transmits uplink data to the base station. Generally, the RF circuit 810 includes, but is not limited to, an antenna, at least one amplifier, a transceiver, a coupler, a low noise amplifier (LNA), a duplexer, and the like. In addition, the RF circuit 810 may also communicate with a network and another device through wireless communication. The wireless communication may use any communication standard or protocol, including but not limited to global system for mobile communications (GSM), general packet radio service (GPRS), code division multiple access (CDMA), wideband code division multiple access (WCDMA), long term evolution (LTE), email, short messaging service (SMS), and the like.

The memory 820 may be configured to store a software program and a module. The processor 880 runs the software program and the module that are stored in the memory 820, to implement various functional applications and data processing of the mobile phone. The memory 820 may mainly include a program storage area and a data storage area. The program storage area may store an operating system, an application required by at least one function (for example, a sound playing function and an image playing function), or the like. The data storage area may store data (for example, audio data and a phone book) created according to use of the mobile phone. In addition, the memory 820 may include a high speed random access memory, and may further include a non-volatile memory, such as at least one magnetic disk storage device, a flash memory, or another volatile solid-state storage device.

The input unit 830 may be configured to receive inputted digit or character information, and generate a key signal input related to the user setting and function control of the mobile phone. Specifically, the input unit 830 may include a touch panel 831 and another input device 832. The touch panel 831, also referred to as a touchscreen, may collect a touch operation of a user on or near the touch panel (such as an operation of a user on or near the touch panel 831 by using any suitable object or accessory such as a finger or a stylus), and drive a corresponding connection apparatus according to a preset program. In some embodiments, the touch panel 831 may include two parts: a touch detection apparatus and a touch controller. The touch detection apparatus detects a touch orientation of the user, detects a signal brought by the touch operation, and transmits the signal to the touch controller. The touch controller receives touch information from the touch detection apparatus, converts the touch information into a contact coordinate, then sends the contact coordinate to the processor 880, and can receive and execute a command sent by the processor 880. In addition, the touch panel 831 may be implemented by using various types, such as a resistive type, a capacitive type, an infrared type, and a surface acoustic wave type. In addition to the touch panel 831, the input unit 830 may further include the another input device 832. Specifically, the another input device 832 may include, but is not limited to, one or more of a physical keyboard, a functional key (such as a volume control key or a switch key), a track ball, a mouse, and a joystick.

The display unit 840 may be configured to display information inputted by the user or information provided for the user, and various menus of the mobile phone. The display unit 840 may include a display panel 841. In some embodiments, the display panel 841 may be configured in the form of a liquid crystal display (LCD), an organic light-emitting diode (OLED), or the like. Further, the touch panel 831 may cover the display panel 841. After detecting a touch operation on or near the touch panel, the touch panel 831 transfers the touch operation to the processor 880, to determine a type of a touch event. Then, the processor 880 provides a corresponding visual output on the display panel 841 according to the type of the touch event. Although in FIG. 20, the touch panel 831 and the display panel 841 are used as two separate parts to implement input and output functions of the mobile phone, in some embodiments, the touch panel 831 and the display panel 841 may be integrated to implement the input and output functions of the mobile phone.

The mobile phone may further include at least one sensor 850 such as an optical sensor, a motion sensor, and other sensors. Specifically, the optical sensor may include an ambient light sensor and a proximity sensor, where the ambient light sensor may adjust luminance of the display panel 841 according to the luminance of the ambient light, and the proximity sensor may switch off the display panel 841 and/or backlight when the mobile phone is moved to the ear. As one type of motion sensor, an acceleration sensor can detect magnitude of accelerations in various directions (generally on three axes), may detect magnitude and a direction of the gravity when static, and may be applied to an application that recognizes the attitude of the mobile phone (for example, switching between landscape orientation and portrait orientation, a related game, and magnetometer attitude calibration), a function related to vibration recognition (such as a pedometer and a knock), and the like. Other sensors, such as a gyroscope, a barometer, a hygrometer, a thermometer, and an infrared sensor, which may be configured in the mobile phone, are not further described herein.

The audio circuit 860, a speaker 861, and a microphone 862 may provide audio interfaces between the user and the mobile phone. The audio circuit 860 may convert received audio data into an electrical signal and transmit the electrical signal to the speaker 861. The speaker 861 converts the electrical signal into a sound signal and outputs the sound signal. In addition, the microphone 862 converts a collected sound signal into an electrical signal. After receiving the electrical signal, the audio circuit 860 converts the electrical signal into audio data, and then outputs the audio data. After being processed by the processor 880, the audio data is transmitted through the RF circuit 810 to, for example, another mobile phone or the audio data is outputted to the memory 820 for further processing.

Wi-Fi is a short distance wireless transmission technology. The mobile phone may help, by using the Wi-Fi module 870, a user to receive and transmit an email, browse a web page, access stream media, and the like. This provides wireless broadband Internet access for the user. Although FIG. 20 shows the Wi-Fi module 870, it may be understood that the Wi-Fi module is not a necessary component of the mobile phone, and the Wi-Fi module may be omitted as required provided that the scope of the essence of the present disclosure is not changed.

The processor 880 is a control center of the mobile phone, and is connected to various parts of the entire mobile phone by using various interfaces and lines. By running or executing the software program and/or the module stored in the memory 820, and invoking data stored in the memory 820, the processor 880 executes various functions of the mobile phone and performs data processing, thereby monitoring the entire mobile phone. In some embodiments, the processor 880 may include one or more processing units. In some embodiments, the processor 880 may integrate an application processor and a modem. The application processor mainly processes an operating system, a user interface, an application, and the like. The modem mainly processes wireless communication. It may be understood that the foregoing modem may alternatively not be integrated into the processor 880.

The mobile phone further includes the power supply 890 (such as a battery) for supplying power to the components. In some embodiments, the power supply may be logically connected to the processor 880 by using a power management system, thereby implementing functions such as charging, discharging and power consumption management by using the power management system.

Although not shown in the figure, the mobile phone may further include a camera, a Bluetooth module, and the like, which are not further described herein.

In this embodiment of the present disclosure, the processor 880 included in the terminal device further has the following functions:

obtaining an original image and an AE set, the original image being an image having not been labeled, the AE set including N AEs, N being an integer greater than or equal to 1;

obtaining an encoded image set corresponding to the original image by using the AE set, the encoded image set including N encoded images, the encoded images being corresponding to the AEs;

obtaining the encoded image set and a segmentation result set corresponding to the original image by using an image segmentation network, the image segmentation network including M image segmentation sub-networks, and the segmentation result set including [(N+1)*M] segmentation results, M being an integer greater than or equal to 1; and determining uncertainty corresponding to the original image according to the segmentation result set, the uncertainty being used for determining whether the original image is a to-be-labeled image.

A person skilled in the art can clearly understand that for convenience and conciseness of description, for specific working processes of the foregoing described system, apparatus and unit, refer to the corresponding processes in the foregoing method embodiments, and details are not described herein.

In the several embodiments provided in the present disclosure, it is to be understood that the disclosed system, apparatus, and method may be implemented in other manners. For example, the described apparatus embodiment is merely exemplary. For example, the unit division is merely a logical function division and may be other division during actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electric, mechanical, or other forms.

The units described as separate components may or may not be physically separated, and the components displayed as units may or may not be physical units, and may be located in one place or may be distributed over a plurality of network units. Some or all of the units may be selected according to actual requirements to achieve the objectives of the solutions of the embodiments.

In addition, functional units in the embodiments of the present disclosure may be integrated into one processing unit, or each of the units may exist alone physically, or two or more units may be integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions of the present disclosure essentially, or the part contributing to the related technology, or all or some of the technical solutions may be implemented in the form of a software product. The computer software product is stored in a storage medium and includes several instructions for instructing a computer device (which may be a personal computer, a server, a network device, or the like) to perform all or some of the steps of the methods described in the embodiments of the present disclosure. The foregoing storage medium includes: any medium that can store program code, such as a USB flash drive, a removable hard disk, a read-only memory (read-only memory, ROM), a random access memory (random access memory, RAM), a magnetic disk or an optical disc.

The foregoing embodiments are merely intended for describing the technical solutions of the present disclosure, but not for limiting the present disclosure. Although the present disclosure is described in detail with reference to the foregoing embodiments, a person of ordinary skill in the art is to understand that modifications may be made to the technical solutions described in the foregoing embodiments or equivalent replacements may be made to some technical features thereof, without departing from the spirit and scope of the technical solutions of the embodiments of the present disclosure.

What is claimed is:

1. A method for determining a target image, performed by a computing device, the method comprising:
   obtaining an original image and an autoencoder (AE) set, the original image being an image having not been labeled, the AE set comprising N AEs of at least two types, N being an integer greater than 1;
   obtaining an encoded image set corresponding to the original image by using the AE set, the encoded image set comprising N encoded images, the encoded images being corresponding to the AEs, wherein a first encoded image obtained using a first AE in the AE set is different from a second encoded image obtained using a second AE in the AE set, the first AE and the second AE belonging to two different types in the at least two types;
   obtaining the encoded image set and a segmentation result set corresponding to the original image by using an image segmentation network, the image segmentation network comprising M image segmentation sub-networks, and the segmentation result set comprising [(N+1)*M] segmentation results, M being an integer greater than 1, wherein a first image segmentation sub-network in the M image segmentation sub-networks is different from a second image segmentation sub-network in the M image segmentation sub-networks;
   determining labeling uncertainty corresponding to the original image according to entropy sets corresponding to pixels in the original image; and
   determining whether the original image is a target image according to the labeling uncertainty,
   wherein determining the labeling uncertainty according to the entropy sets corresponding to the pixels in the original image comprises: obtaining an entropy set of a pixel in the original image by:
      obtaining a grayscale value corresponding to the pixel in the original image; and
      determining the entropy set corresponding to the pixel according to the segmentation result set and the grayscale value corresponding to the pixel in the original image, the entropy set of the one pixel comprising [(N+1)*M] entropies.

2. The method according to claim 1, wherein the obtaining the encoded image set and a segmentation result set corresponding to the original image by using an image segmentation network comprises:
   obtaining a first segmentation result by using the first image segmentation sub-network, the first segmentation result comprising (N+1) first segmentation sub-results, the (N+1) first segmentation sub-results being corresponding to the encoded images in the encoded image set and the original image; and
   obtaining a second segmentation result by using the second image segmentation sub-network, the second segmentation result comprising (N+1) second segmentation sub-results, the (N+1) second segmentation sub-results being corresponding to the encoded images in the encoded image set and the original image.

3. The method according to claim 1, wherein after the determining labeling uncertainty corresponding to the original image, the method further comprises:
   determining whether the labeling uncertainty is greater than or equal to an uncertainty threshold; and
   determining the original image as the target image when the labeling uncertainty is greater than or equal to the uncertainty threshold.

4. The method according to claim 1, wherein before the obtaining an original image and an AE set, the method further comprises:
   obtaining a training image, the training image being an image having been labeled;
   encoding the training image by using an encoder of an AE to be trained to obtain an encoded result;
   decoding the encoded result by using a decoder of the AE to obtain a prediction image;
   training the AE by using the training image and the prediction image until a loss function converges, to obtain an AE model parameter; and
   generating the AE according to the AE model parameter, the AE being one AE in the AE set.

5. The method according to claim 1, wherein before the obtaining the encoded image set and a segmentation result set corresponding to the original image by using an image segmentation network, the method further comprises:
   obtaining a training image, the training image being an image having been labeled;
   obtaining a prediction image corresponding to the training image by using an image segmentation sub-network to be trained;
   training the image segmentation sub-network by using the training image and the prediction image until a loss function converges, to obtain a network model parameter; and
   generating the image segmentation sub-network according to the network model parameter, the image segmentation sub-network being one image segmentation sub-network in the image segmentation network.

6. The method according to claim 1, wherein:
   each of the M image segmentation sub-networks is used to obtain (N+1) segmentation results, to generate a total of the [(N+1)*M] segmentation results in the segmentation result set.

7. The method according to claim 6, wherein:
   the [(N+1)*M] entropies of the one pixel corresponding to the pixel comprise (N+1) entropies corresponding to the (N+1) segmentation results of each of the M image segmentation sub-networks.

8. The method according to claim 1, wherein the at least two types of AEs include two or more of: a sparse AE, a variational AE (VAE), a contractive AE (CAE), or a denoising AE (DAE).

9. An apparatus for determining a target image, comprising at least one memory and at least one processor, the at least one memory being configured to store a program; the at least one processor being configured to execute the program in the at least one memory to:

obtain an original image and an autoencoder (AE) set, the original image being an image having not been labeled, the AE set comprising N AEs of at least two types, N being an integer greater than 1;

obtain an encoded image set corresponding to the original image by using the AE set, the encoded image set comprising N encoded images, the encoded images being corresponding to the AEs, wherein a first encoded image obtained using a first AE in the AE set is different from a second encoded image obtained using a second AE in the AE set, the first AE and the second AE belonging to two different types in the at least two types;

obtain the encoded image set and a segmentation result set corresponding to the original image by using an image segmentation network, the image segmentation network comprising M image segmentation sub-networks, and the segmentation result set comprising $[(N+1)*M]$ segmentation results, M being an integer greater than 1, wherein a first image segmentation sub-network in the M image segmentation sub-networks is different from a second image segmentation sub-network in the M image segmentation sub-networks;

determine a labeling uncertainty corresponding to the original image according to variances of pixels in the original image and a total quantity of the pixels; and determine whether the original image is a target image according to the labeling uncertainty, wherein determining the labeling uncertainty according to the variances of pixels in the original image and the total quantity of the pixels comprises: obtaining a variance of the pixel in the original image by:
obtaining a grayscale value corresponding to the pixel in each of the segmentation results, and
determining the variance of the one pixel based on the $[(N+1)*M]$ segmentation results in the segmentation result set corresponding to the one pixel and according to the grayscale value corresponding to the pixel in the each segmentation result.

10. The apparatus according to claim 9, wherein the at least one processor is further configured to:
obtain a first segmentation result by using the first image segmentation sub-network, the first segmentation result comprising (N+1) first segmentation sub-results, the (N+1) first segmentation sub-results being corresponding to the encoded images in the encoded image set and the original image; and
obtain a second segmentation result by using the second image segmentation sub-network, the second segmentation result comprising (N+1) second segmentation sub-results, the (N+1) second segmentation sub-results being corresponding to the encoded images in the encoded image set and the original image.

11. The apparatus according to claim 9, wherein the at least one processor is further configured to:
determine whether the labeling uncertainty is greater than or equal to an uncertainty threshold; and
determine the original image as the target image when the labeling uncertainty is greater than or equal to the uncertainty threshold.

12. The apparatus according to claim 9, wherein the at least one processor is further configured to:
obtain a training image before obtaining the original image and the AE set, the training image being an image having been labeled;
encode, by using an encoder of an AE to be trained, the training image to obtain an encoded result;
decode, by using a decoder of the AE, the encoded result to obtain a prediction image;
train the AE by using the training image and the prediction image decoded by the decoding module until a loss function converges, to obtain an AE model parameter; and
generate the AE according to the AE model parameter, the AE being one AE in the AE set.

13. The apparatus according to claim 9, wherein the at least one processor is further configured to:
obtain a training image before obtaining the encoded image set and the segmentation result set corresponding to the original image by using the image segmentation network, the training image being an image having been labeled;
obtain a prediction image corresponding to the training image by using an image segmentation sub-network to be trained;
train the image segmentation sub-network by using the training image and the prediction image until a loss function converges, to obtain a network model parameter; and
generate the image segmentation sub-network according to the network model parameter, the image segmentation sub-network being one image segmentation sub-network in the image segmentation network.

14. The apparatus according to claim 9, wherein determining the labeling uncertainty according to the variances of pixels in the original image and the total quantity of the pixels comprises:
determining the labeling uncertainty by dividing a sum of the variances of pixels in the original image with the total quantity of the pixels.

15. A non-transitory computer-readable storage medium, comprising instructions, the instructions, when run on a computer, causing the computer to perform:
obtaining an original image and an autoencoder (AE) set, the original image being an image having not been labeled, the AE set comprising N AEs of at least two types, N being an integer greater than 1;
obtaining an encoded image set corresponding to the original image by using the AE set, the encoded image set comprising N encoded images, the encoded images being corresponding to the AEs, wherein a first encoded image obtained using a first AE in the AE set is different from a second encoded image obtained using a second AE in the AE set, the first AE and the second AE belonging to two different types in the at least two types;
obtaining the encoded image set and a segmentation result set corresponding to the original image by using an image segmentation network, the image segmentation network comprising M image segmentation sub-networks, and the segmentation result set comprising $[(N+1)*M]$ segmentation results, M being an integer greater than 1, wherein a first image segmentation sub-network in the M image segmentation sub-networks is different from a second image segmentation sub-network in the M image segmentation sub-networks;
determining labeling uncertainty corresponding to the original image according to entropy sets corresponding to pixels in the original image; and
determining whether the original image is a target image according to the labeling uncertainty,
wherein determining the labeling uncertainty according to the entropy sets corresponding to the pixels in the original image comprises: obtaining an entropy set of a pixel in the original image by:
  obtaining a grayscale value corresponding to the pixel in the original image; and
  determining the entropy set corresponding to the pixel according to the segmentation result set and the grayscale value corresponding to the pixel in the original image, the entropy set of the one pixel comprising $[(N+1)*M]$ entropies.

16. The storage medium according to claim 15, wherein the obtaining the encoded image set and a segmentation result set corresponding to the original image by using an image segmentation network comprises:
  obtaining a first segmentation result by using the first image segmentation sub-network, the first segmentation result comprising (N+1) first segmentation sub-results, the (N+1) first segmentation sub-results being corresponding to the encoded images in the encoded image set and the original image; and
  obtaining a second segmentation result by using the second image segmentation sub-network, the second segmentation result comprising (N+1) second segmentation sub-results, the (N+1) second segmentation sub-results being corresponding to the encoded images in the encoded image set and the original image.

* * * * *